United States Patent [19]

Lee et al.

[11] Patent Number: 4,803,280

[45] Date of Patent: Feb. 7, 1989

[54] SUBSTITUTED 1,2,3-THIA-DIAZOLE-4-THIOLATES

[75] Inventors: Ving J. Lee, Monsey; William V. Curran, Pearl River, both of N.Y.

[73] Assignee: American Cyanamid Company, Wayne, N.J.

[21] Appl. No.: 883,189

[22] Filed: Jul. 8, 1986

[51] Int. Cl.$^4$ ............................................. C07D 285/06
[52] U.S. Cl. .................................................... 548/127
[58] Field of Search .................................. 548/127, 135

[56] References Cited

FOREIGN PATENT DOCUMENTS 0012868 11/1979 European Pat. Off. ............ 548/127

OTHER PUBLICATIONS

Lewis et al., Journ. Med. Chem., 1979, vol. 22, No. 10, pp. 1214–1218.
Adachi et al., Chem. Pharm. Bull., 31(5), 1746–50.

*Primary Examiner*—Robert Gerstl
*Attorney, Agent, or Firm*—Robert P. Raymond

[57] ABSTRACT

Intermediates useful for synthesis of cephalosporins are disclosed, which intermediates are concerned with 1,2,3-thiadiazole-4-thiolates and the preparation of such thiolates.

11 Claims, No Drawings

SUBSTITUTED 1,2,3-THIA-DIAZOLE-4-THIOLATES

SUMMARY OF THE INVENTION

This invention is concerned with 1,2,3-thiadiazole-4-thiolate intermediates which are useful in the preparation of cephalosporanic acid derivatives having antibacterial activity. Further, this invention is concerned with certain intermediates used to prepare such 1,2,3-thiadiazole-4-thiolates as well as processes for their preparation.

In sequence, $N^2$-thioacylcarbazates, $N^2$-thioacylarenesulfonylhydrazides, and $N^3$-thioacylsemicarbazides of the formula:

$$R_1-CH_2\overset{S}{\overset{\|}{C}}-NHNHCOR_2$$

where $R_1$ is selected from the group consisting of hydrogen; alkyl($C_1$-$C_6$); polyfluorinated alkyls($C_1$-$C_6$); phenyl; (multisubstituted)phenyl wherein the substituents are selected from alkyl($C_1$-$C_6$), alkoxy($C_1$-$C_3$), chloro, fluoro and trifluoromethyl; naphthyl; thienyl; phenylthio; tetrahydropyranyl; benzyl; and —$COOC_2H_5$; and $R_2$ is selected from the group consisting of amino and alkoxy($C_1$-$C_3$), are used to produce N-acylthiohydrazonate esters (E and Z isomers) of the formula:

$$R_1-CH_2\overset{S-R_3}{\overset{|}{C}}=NNHCOR_2$$
(E and Z isomers)

where $R_1$ and $R_2$ are as described above and $R_3$ is —$CH_2CH_2COOR_4$, where $R_4$ is alkyl($C_1$-$C_3$).

These N-acylthiohydrazonate esters are used to make either alkyl 3-(1,2,3-thiadiazol-4-ylthio)propionates of the formula:

[structure: 1,2,3-thiadiazole with SCH$_2$CH$_2$COOR$_4$ and R$_1$ substituents]

where $R_1$ is as described above and $R_4$ is alkyl($C_1$-$C_3$) or 4-(substituted thio)-1,2,3-thiadiazoles of the formula:

[structure: 1,2,3-thiadiazole with SR$_5$ and R$_1$ substituents]

where $R_1$ is as described above and $R_5$ is selected from the group consisting of alkyl($C_1$-$C_3$); phenyl; alkenyl(-$C_3$-$C_6$); —$CH_2COOC_2H_5$; —$C(CH_3)_2COOC_2H_5$ and —$CH_2CH_2CN$.

Either the alkyl 3-(1,2,3-thiadiazol-4-ylthio)propionates or the 4-(substituted thio)-1,2,3-thiadiazoles are then used to produce the 1,2,3-thiadiazole-4-thiolates, which are the end products of this invention and are represented by the formula:

[structure: 1,2,3-thiadiazole with S$^⊖$M$^⊕$ and R$_1$ substituents]

where $R_1$ is as described above and M is sodium or potassium.

DESCRIPTION OF THE INVENTION

The compounds of this invention may be prepared according to the following reaction schemes:

Scheme I $$R_1-CH_2\overset{S}{\overset{\|}{C}}SCH_2COO-\text{alkyl} + NH_2NHCOR_2$$
$$1 \qquad\qquad\qquad\qquad 2$$

$$\downarrow$$

$$R_1CH_2\overset{S}{\overset{\|}{C}}-NHNHCOR_2$$
$$3$$

According to Scheme I a (2-substituted-1-thioxoalkyl)thioglycolic acid 1, where $R_1$ is hydrogen, phenyl or 4-tert-butylphenyl is reacted with an alkyl hydrazine carboxylate 2-, where $R_2$ is methoxy or ethoxy, in a solvent such as chloroform or dichloromethane, at reflux, giving the $N^2$-thiocylcarbazates 3 which are purified by conventional chromatography.

Scheme II $$R_1-\overset{O}{\overset{\|}{C}}-CH_3 + HN\diagdown\text{(piperidine)} + S \rightarrow R_1-CH_2-\overset{S}{\overset{\|}{C}}-N\diagdown\text{(piperidine)}$$
$$4 \qquad\qquad\qquad\qquad\qquad\qquad 5$$

$$\downarrow BrCH_2COOH$$

$$R_1CH_2\overset{S}{\overset{\|}{C}}-SCH_2COOH \xleftarrow{H_2S} R_1-CH_2\overset{SCH_2COOH}{\overset{|}{C}}=N^⊕\diagdown\text{(piperidine)} Br^⊖$$
(or methyl or ethyl esters)
$$7 \qquad\qquad\qquad\qquad 6$$
$$+$$
$$NH_2NHCOR_2$$
$$2$$

$$\downarrow$$

$$R_1-CH_2\overset{S}{\overset{\|}{C}}-NHNHCOR_2$$
$$3$$

According to Scheme II, a substituted methyl ketone 4, where $R_1$ is 4-t-butylphenyl, 4-methoxyphenyl, 3,4,5-trimethoxyphenyl, naphthyl, thienyl or 3-methoxyphenyl is heated with piperidine and sulfur giving the piperidine derivative 5 which is then reacted with bromoacetic acid in an organic solvent giving the piperidinium bromide derivative 6 which is reacted with hydrogen sulfide in an alkanol, at 0°–35° C., giving the acetic acid derivative 7, or alkyl esters thereof, which is then reacted with an alkyl hydrazine carboxylate 2, where $R_2$ is methoxy or ethoxy in a solvent such as dichloromethane, at reflux giving the $N^2$-thioacylcarbazates 3 which are purified by chromatography.

Scheme III

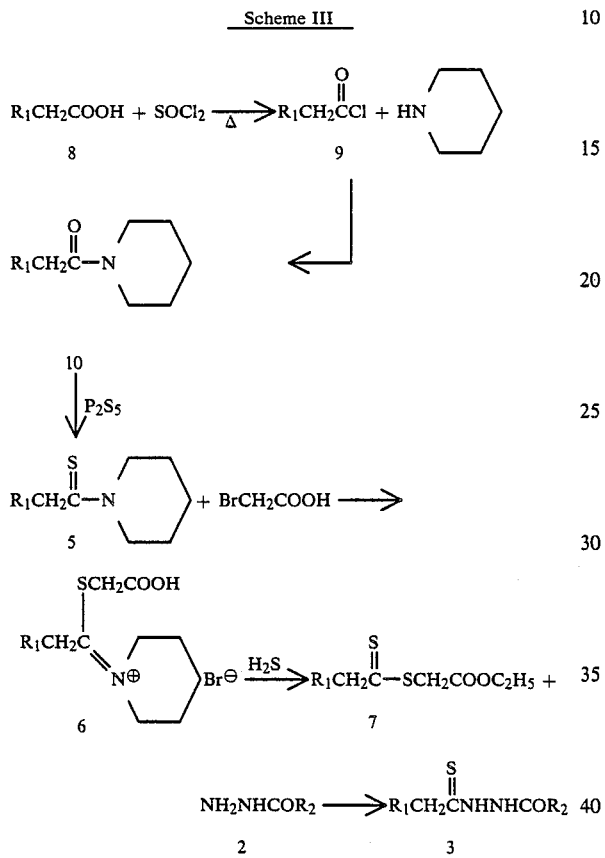

According to Scheme III an acetic acid derivative 8, where $R_1$ is 4-chlorophenyl, 4-fluorophenyl, 3-(trifluoromethyl)phenyl, $C_2H_5OOC-$, phenylthio or 2-tetrahydropyranyl, is reacted with thionyl chloride in a solvent such as benzene at reflux giving the acyl chloride derivative 9 which is then reacted with piperidine in pyridine and ether giving the piperidine derivative 10 which is reacted with phosphorus pentasulfide in pyridine at reflux giving piperidine derivative 5 followed by reaction as described in Scheme II to produce 3.

Scheme IV

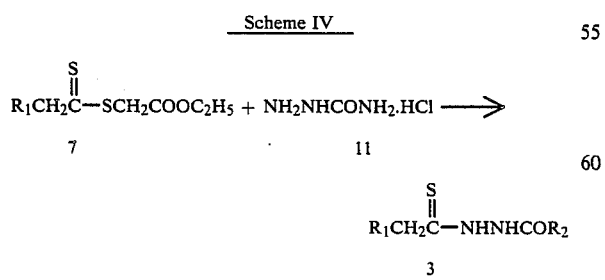

According to Scheme IV, an acetic acid ester 7, where $R_1$ is alkyl($C_1$–$C_6$) or benzyl is reacted with semicarbazide hydrochloride 11 and anhydrous sodium acetate in ethanol with heat giving the compounds 3 where $R_2$ is $NH_2$.

Scheme V

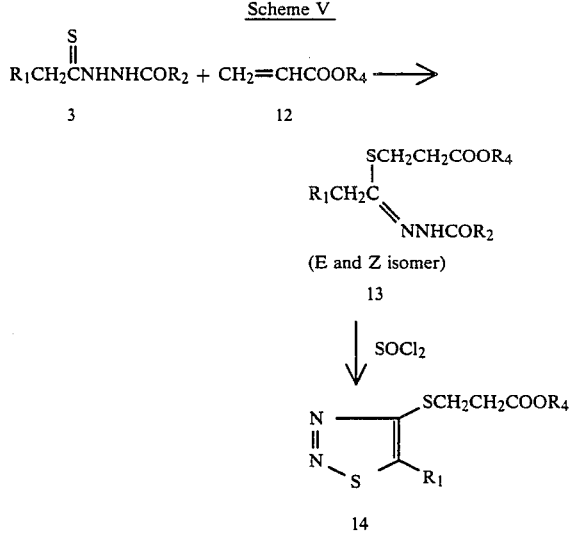

According to Scheme V an $N^2$-thioacylcarbazate ester 3, where $R_1$ is alkyl($C_1$–$C_6$), phenyl, benzyl, 3-methoxyphenyl, 4-methoxyphenyl, 3,4,5-trimethoxyphenyl, 4-t-butylphenyl, naphthyl, thienyl, 4-chlorophenyl, 4-fluorophenyl, 3-(trifluoromethyl)phenyl, phenylthio or tetrahydropyranyl and $R_2$ is alkoxy($C_1$–$C_3$) is reasted with an acrylate 12 where $R_4$ is methyl or ethyl and triethylamine in benzene, at reflux giving a hydrazinecarboxylic acid ester 13 (E and Z isomers) which is then reacted with thionyl chloride in benzene at reflux, giving the propanoic acid esters 14.

Scheme VI

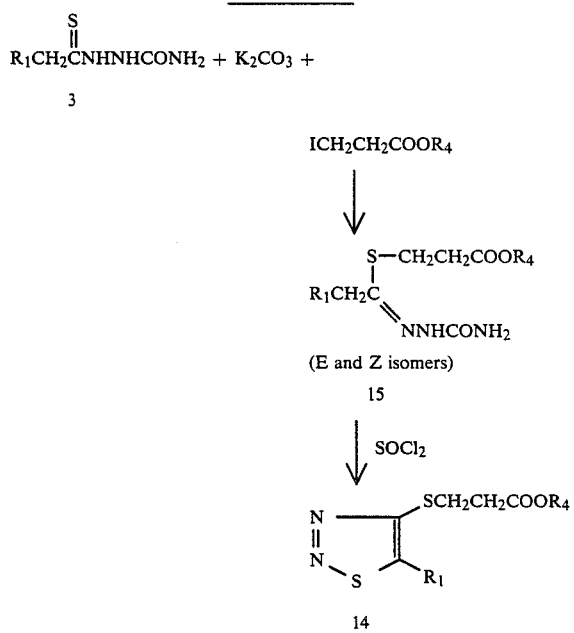

According to Scheme VI a substituted thioacylsemicarazide 3, where $R_1$ is alkyl($C_1$–$C_6$) is reacted with potassium carbonate and an alkyl 3-iodopropionate in acetone at reflux, giving a hydrazono propanoic acid derivative 15 (E and Z isomers), which is then reacted with thionyl chloride in dichloromethane, giving the 1,2,3thiadiazole derivatives 14.

ride giving the 4-(methylthio)-,1,2,3-thiadiazole derivatives 20.

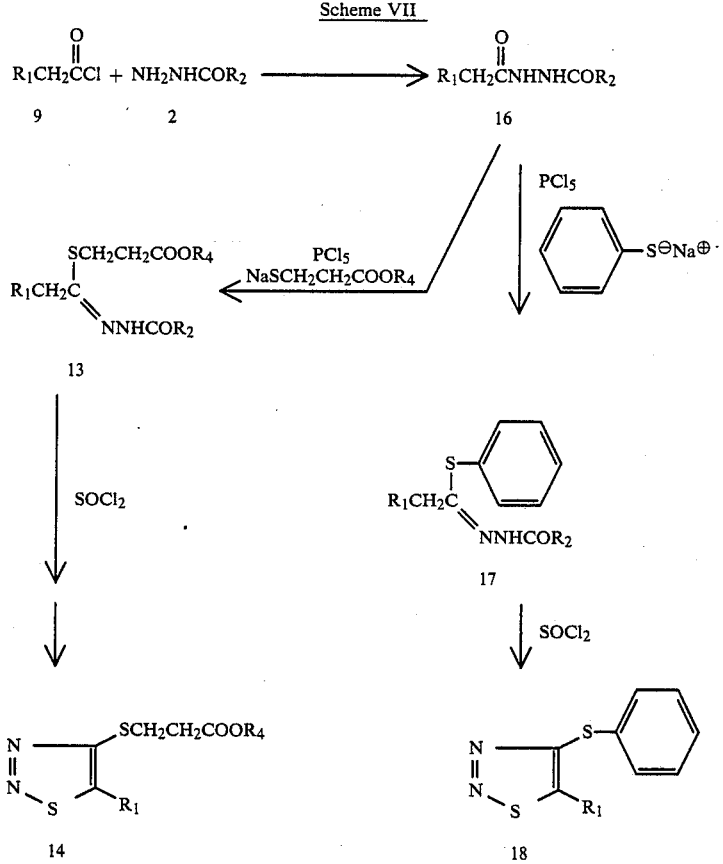

According to Scheme VII an acetyl chloride 9, where $R_1$ is hydrogen or t-butyl is reacted with an alkyl hydrazine caroxylate 2, where $R_2$ is methyl or ethyl in pyridine and dichloromethane at 0°–5° C., giving hydrazine derivative 16 which is reacted with phosphorus pentachloride in chloroform, followed by reaction with sodium thiophenoxide in tetrahydrofuran, giving phenylthio derivative 17 which is then reacted with thionyl chloride in chloroform at reflux giving 4-(phenylthio)-1,2,3-thiadiazole 18.

Alternatively, reaction of 16 with phosphorus pentachloride in chloroform, followed by reaction with sodium (or potassium) ethyl (or methyl)-propionate-3-thiolate in tetrahydrofuran, giving derivative 13 which is then reacted with thionyl chloride in methylene chloride at reflux giving 1,2,3-thiadiazoles 14.

Scheme VIII

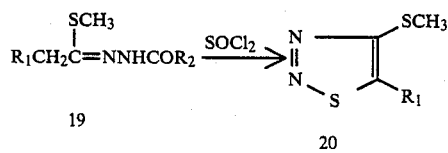

According to Scheme VIII a methylthio hydrazine derivative 19, where $R_1$ is thienyl or 4-methoxyphenyl and $R_2$ is methyl or ethyl is reacted with thionyl chloride giving the 4-(methylthio)-1,2,3-thiadiazole derivatives 20.

According to Scheme IX a [(1,2,3-thiadiazol-4-yl)thio]propanoic acid ester 14, where $R_1$ is as disclosed in this invention and $R_4$ is methyl or ethyl is reacted with sodium or potassium alkoxide in an alkanol, giving the products 21.

This invention will be described in detail in conjunction with the following non-limiting examples.

EXAMPLE 1

2-(1-Thioxoethyl)hydrazinecarboxylic acid, methyl ester

A mixture of 129 g of 2-(1-thioxoethyl)thioglycolic acid, ethyl ester, 67.5 g of methyl hydrazinocarboxylate and 500 ml of chloroform was heated at reflux for 8 hours, then concentrated in vacuo. The oily residue was concentrated further under high vacuum, giving a yellow oil. This oil was dissolved in 500 ml of dichloromethane and passed through a bed of hydrous magnesium silicate, washing with additional dichloromethane. The resulting light yellow oil was crystallized from toluene-methylcyclohexane, giving 70 g of the desired compound as ivory crystals, mp 99°–100.5° C. Proton nuclear magnetic resonance (δ [ppm], CDCl$_3$) 90 MHz: 2.42 (s, 3H, CH$_3$CS); 3.76 (s, 3H, OCH$_3$); 8.55 (bs, 1H, NH); 9.56 (bs, 1H, NH).

EXAMPLE 2

2-(1-Thioxoethyl)hydrazinecarboxylic acid, ethyl ester

A mixture of 110 g of 2-(1-thioxoethyl)thioglycolic acid, ethyl ester, 65.2 g of ethyl hydrazinocarboxylate and 500 ml of dichloromethane was heated at reflux for 3 hours, then concentrated in vacuo. The oily residue was concentrated further under high vacuum, giving a yellow oil. This oil was dissolved in 500 ml of dichloromethane and passed through a bed of hydrous magnesium silicate, washing with additional dichloromethane. The resulting light yellow oil was crystallized from diisopropyl ether giving a 79% yield of the desired compound as ivory crystals, mp 54.0°–57.5° C. Proton nuclear magnetic resonance (δ [ppm], CDCl$_3$) 90 MHz: 1.30 (t, 3 H, J=7.4 Hz, CH$_3$CH$_2$); 2.55 (s, 3H, CH$_3$CS); 4.25 (q, 2H, CH$_2$CH$_3$); 8.75 (bs, 1H, NH); 10.35 (bs, NH).

EXAMPLE 3

2-(3,3-Dimethyl-1-thioxobutyl)hydrazinecarboxylic acid, methyl ester

A mixture of 122 g of 2-(3,3-dimethyl-1-thioxobutyl)thioglycolic acid, methyl ester, 54.3 g of methyl hydrazinocarboxylate and 750 ml of dichloromethane was heated at reflux for one hour, then concentrated in vacuo. The orange residue was taken up in ether, washed twice with water and then three times with 0.5N sodium hydroxide. The alkaline extracts were combined, back washed with ether and then acidified with 2N hydrochloric acid to pH 3. The product was extracted into ether and worked up to give a light orange viscous oil. This oil was taken up in dichloromethane, applied to a 60 mm×600mm, 60 g column of silica gel (200–400 mesh) packed in dichloromethane and eluted with a gradient of 0–10% methanol in dichloromethane. The desired fractions were collected, giving 93.0 g of a light yellow oil. This oil was crystallized from methylcyclohexane, giving 91.0 g (81% yield) of the desired compound as ivory crystals, mp 72.5°–73° C. Proton nuclear magnetic resonance (δ[ppm], CDCl$_3$) 90 MHz: 1.07 (s, 9H, t-butyl); 2.63 (s, 2H, CH$_3$CS); 3.80 (s, 3H, OCH$_3$); 8.75 (bs, 1H, NH); 9.65 (bs, 1H, NH).

EXAMPLE 4

2-(2-Phenyl-1-thioxoethyl)hydrazinecarboxylic acid, methyl ester

A mixture of 86.0 g of 2-(2-phenyl-1-thioxoethyl)thioglycolic acid, 195 ml of 2N sodium hydroxide and 100 ml of water was added dropwise to a suspension of 50 g of methyl hydrazinocarboxylate in 200 ml of water with vigorous stirring. Stirring was continued overnight, then the mixture was extracted twice with ether. The extracts were combined, washed successively with 5% aqueous sodium bicarbonate (twice), water and saturated aqueous sodium chloride, dried and concentrated in vacuo. The dark orange oil was purified by percolation through a bed of hydrous magnesium silicate with dichloromethane. The resulting pale yellow oil was chromatographed on a 70×850 mm dry column of silica gel, eluting with dichloromethane. The resulting oil was crystallized from toluene-hexane, giving 42.6 g of the desired compound as yellow crystals, mp 93.5°–94° C. Proton nuclear magnetic resonance (δ[ppm], CDCl$_3$) 90 MHz: 3.79 (s, 3H, OCH$_3$); 4.11 (s, 2H, CH$_3$CS); 7.33 (bs, 5H, C$_6$H$_5$); 8.65 (bs, 1H, NH); 9.55 (bs, 1H, NH).

EXAMPLE 5

2-[2-(4-Methylphenyl)-1-thioxoethyl]hydrazinecarboxylic acid, methyl ester

A mixture of 37.0 g of 2-[2-(4-methylphenyl)-1-thioxoethyl]thioglycolic acid, 18.2 g of methyl hydrazinocarboxylate and 250 ml of dichloromethane was heated at reflux for one hour and then evaporated in vacuo. The residue was concentrated at high vacuum and 45° C. for one hour. The oily residue was chromatographed on a 75×800mm dry column of silica gel, eluting with dichloromethane. The desired fractions were pooled and the solid crystallized from toluene-hexane, giving 30 g of the desired compound as off-white needles, mp 104.5°–105° C. Proton nuclear magnetic resonance (δ[ppm], CDCl$_3$) 90 MHz: 2.38 (s, CH$_3$); 3.79 (s, 3H, OCH$_3$); 4.07 (s, 2H, CH$_2$CS); 7.23 (s, 4H, C$_6$H$_4$); 8.68 (bs, 1H, NH); 9.52 (bs, 1H, NH).

EXAMPLE 6

2-[2-[4-(1,1-Dimethylethyl)phenyl]-1-thioxoethyl]-hydrazinecarboxylic acid, methyl ester A mixture of 176.1 g of 4-(tert-butyl)acetophenone, 128 g of piperidine and 48.5 g of powdered sulfur was heated at reflux for 14 hours, then cooled and concentrated in vacuo. The residue was taken up in a mixture of ether and water and then extracted twice with ether. The organic extracts were combined, washed successively with water, 5% hydrochloric acid, water and saturated aqueous sodium chloride, then dried and concentrated. The resulting oil was diluted with 1.5 liters of hexane and cooled at −60° to −75° C. for 3 hours. The resulting solid was collected, washed with cyclohexane, then dissolved in dichloromethane, decolorized with charcoal and crystallized from cyclohexane, giving 138 g of N-[2-(4-t-butylphenyl)-1-thioxoethyl]piperidine.

A mixture of 137.6 g of the above compound, 76.5 g of bromoacetic acid and 500 ml of benzene was stirred overnight and then diluted with 1.5 liters of ether. The solid was collected, washed with ether and dried in vacuo, giving 1-[1-[(carboxymethyl)thio]-2-(4-t-butylphenyl)ethylidene]piperidinium bromide.

A suspension of 124.2 g of the above compound in 500 ml of ethanol was treated with gaseous hydrogen sulfide at 0° C. for 5 hours, then stored overnight at 0° C. The solvent was removed in vacuo and the semi-solid suspended in 700 ml of dry ether, then filtered. The filter cake was washed with ether to remove all coloration. The combined filtrate and washings were extracted three times with 0.1N sodium hydroxide. The combined alkaline extract was acidified and then extracted twice with ether. The organic extracts were combined, washed with water and saturated sodium chloride, dried and concentrated in vacuo, giving an oil.

Trituration with ligroin gave 45.0 g of 2-[2-[4-(1,1dimethylethyl)phenyl]-1-thioxoethyl]thioglycolic acid.

A solution of 40 g of the above compound in 145 ml of 1N sodium hydroxide with 18.1 g of methyl hydrazinocarboxylate was stirred overnight, then adjusted to pH 6 with 0.1N hydrochloric acid and extracted twice with dichloromethane. The extracts were combined, washed with water, then saturated aqueous sodium chloride, dried and concentrated in vacuo. The resulting oil was taken up in dichloromethane and filtered through a bed of hydrous magnesium silicate with dichloromethane. The resulting oil was crystallized from methylcyclohexane, giving 38.5 g of the desired compound as ivory colored crystals, mp 93.5°–94° C. Proton nuclear magnetic resonance ($\delta$[ppm], CDCl$_3$) 90 MHz: 1.30 (s, 9H, t-butyl); 3.74 (s, 3H, OCH$_3$); 4.04 (s, 2H, CH$_2$CS); [7.20 (d, 2H, J=8.0 Hz) and 7.38 (d, 2H) (C$_6$H$_4$)]; 8.54 (bs, 1H, NH); 9.35 (bs, 1H, NH).

EXAMPLE 7

2-[2-(4-Methoxyphenyl)-1-thioxoethyl]hydrazine carboxylic acid, methyl ester

A mixture of 200 g of 4-methoxyacetophenone, 214.5 g of piperidine and 64.5 g of powdered sulfur was reacted as described in Example 6. The product was further reacted with bromoacetic acid and hydrogen sulfide as described in Example 6, giving ethyl 2-[2-(4-methoxyphenyl)1-thioxoethyl]thioglycolate as an orange oil.

A mixture of 50 g of the above ester, 18.2 g of methyl hydrazinocarboxylate and 300 ml of dichloromethane was refluxed for 2 hours, then washed twice with water, once with saturated sodium chloride and dried. The resulting oily residue was concentrated under high vacuum at 50° C. for 2 hours and the semi-solid crystallized from toluene-hexane, giving 36 g of the desired compound as ivory colored crystals, mp 94.5°–95° C. Proton nuclear magnetic resonance ($\delta$[ppm], CDCl$_3$) 90 MHz: 3.78 (s, 3H, OCH$_3$); 3.80 (s, 3H, OCH$_3$); 4.03 (s, 2H, CH$_2$CS); [6.89 (d, 2H, J=8.2 Hz) and 7.21 (d, 2H)(C$_6$H$_4$)]8.60 (bs, 1H, NH); 9.40 (bs, 1H, NH).

EXAMPLE 8

2-[1-Thioxo-2-(3,4,5-trimethoxyphenyl)ethyl hydrazinecarboxylic acid, methyl ester The procedure of Example 6 was repeated using 3,4,5-trimethoxyacetophenone, giving 2-[1-thioxo-2-(3,4,5trimethoxyphenyl)ethyl]thioglycolic acid.

The above compound was reacted as described in Example 7, with methyl hydrazinocarboxylate, giving an 85.0% yield of the desired product as ivory crystals, mp 133.5°–134° C.. Proton nuclear magnetic resonance ($\delta$[ppm], CDCl$_3$) 90 MHz: 3.77 (s, 3H, OCH$_3$); 3.85 (s, 3H, OCH$_3$); 3.87 [s, 6H, OCH$_3$(2X)]; 4.04 (s, 2H, CH$_2$CS); 6.52 (s, 2H, C$_6$H$_2$); 8.51 (bs, 1H, NH); 9.15 (bs, 1H, NH).

EXAMPLE 9

2-[2-(2-Naphthyl)-1-thioxoethyl]hydrazinecarboxylic acid, methyl ester

A mixture of 170.2 g of 2'-acetonaphthone, 51.2 g of sulfur and 136.2 g of piperidine was heated at reflux for 18 hours and then partitioned between dichloromethane and water. The aqueous phase was extracted twice with dichloromethane. The aqueous phases were combined, washed successively with 5% hydrochloric acid, twice with water and then with saturated sodium chloride, dried and filtered through a bed of neutral alumina. The filtrate was concentrated to an oil which was taken up in 700 ml of ether with stirring. This solution was stored in a chillroom overnight and the solid was collected, giving 125 g of 1-[2-(2-naphthyl)-1-thioxoethyl]piperidine, mp 89°–91° C.

A 110 g portion of the above compound was stirred in 1.5 liters of toluene, 61 g of bromoacetic acid was added and this mixture was stirred overnight. The supernatant was decanted, the residue dissolved in 500 ml of dichloromethane and one liter of ether added. The supernatant was decanted and the residue stirred with 300 ml of dichloromethane. The solid was collected, washed with ether and dried in vacuo, giving 54 g of 1-[1-[(carboxymethyl)thio]-2-(2-naphthyl)ethylidene]piperidinium bromide, mp 140°–142° C.

A 40 g portion of the above compoud was slurried in 500 ml of isopropanol, hydrogen sulfide was bubbled into the mixture for 5 hours, then the mixture was alowed to stand overnight and concentrated in vacuo. The residue was slurried in 500 ml of ether and filtered. The filter cake was washed with three 100 ml portions of ether. The filtrate and washings were combined and concentrated in vacuo, giving 23.5 g of 2-[2(2-naphthyl)-1-thioxoethyl]thioglycolic acid.

23.5 g of the above compound was slurried in 90 ml of 1N sodium hydroxide, 130 ml of methanol was added followed by 11.0 g of methyl hydrazinocarboxylate. This mixture was stirred for 3 hours, then diluted with 100 ml of water and the pH adjusted to 5.5. The mixture was extracted twice with dichloromethane, the extracts combined, washed with water and saturated sodium chloride, dried and filtered through hydrous magnesium silicate. The filtrate was concentrated in vacuo, giving 21.3 g of the desired product, mp 129°–131° C. Proton nuclear magnetic resonance ($\delta$[ppm], CDCl$_3$) 90 MHz: 3.75 (s, 3H, OCH$_3$); 4.27 (s, 2H, CH$_2$OS); 7.30–8.00 (m, 7H, C$_{10}$H$_7$); 8.55 (bs, 1H, NH); 9.50 (bs, 1H, NH).

EXAMPLE 10

2[2-(2-Thienyl)-1-thioxoethyl]hydrazinecarboxlic acid, methyl ester

A mixture of 213 g of 2-thiophene acetic acid, 208.2 g of thionyl chloride and one liter of benzene was stirred for 6 hours, then concentrated in vacuo. The residue was taken up in one liter of dry ether, filtered and added dropwise to a cold solution of 301.7 g of dry piperidine and 1.5 liters of dry ether. This mixture was stirred overnight, then diluted with one liter of water and extracted three times with ether. The organic extracts were combined, washed successively: (1) twice with 1N hydrochloric acid, (2) water, (3) twice with 1N sodium hydroxide, (4) water and (5) saturated sodium chloride, and dried. The solution was passed through a bed of hydrous magnesium silicate with additional ether and then concentrated in vacuo. The resulting oil was distilled, giving 250 g of N-(2-thienyl)acetyl piperidine, bp 132°–134° C. (0.5 mmHg).

A mixture of 245 g of the above compound, 245.8 g of Lawesson's reagent and 850 ml of toluene was heated at 70°–78° C. for 12 hours, then cooled and concentrated in vacuo. The residue was taken up in 500 ml of dichloromethane and percolated through a bed of basic alumina with additional solvent. The resulting oil was crystallized from toluenecyclohexane, giving 245 g of N-[2-(2-thienyl)-1-thioxoethyl]piperidine as light yellow needles, mp 51.5°–52° C.

A mixture of 112.7 g of the above compound, 106.5 g of iodomethane and 100 ml of dry ether was stirred for 72 hours. The solid was collected, washed with dry ether and dried in vacuo, giving 175 g of 1-[1-(methylthio)-2-(2-thienyl)ethylidene]piperidinium iodide, mp 135°–140° C.

A suspension of 175 g of the above compound in 650 ml of dry methanol was treated with gaseous hydrogen sulfide for 5 hours, then stored overnight and concentrated in vacuo. The residue was taken up in a mixture of ether and water and the layers separated. The aqueous layer was extracted with ether. The ether solutions were combined washed with saturated sodium chloride, dried, concentrated and distilled, giving 75 g of methyl 2-thiopheneethane(dithioate), bp 98.5–99.5 (0.4–0.5 mmHg) as an orange liquid.

A mixture of 70 g of the above compound, 36 g of methyl hydrazinocarboxylate and 350 ml of dichloromethane was heated at reflux for 2 hours, then cooled and diluted with 500 ml of ether. This solution was extracted three times with saturated aqueous sodium carbonate. The alkaline extracts were combined and back extracted with ether. The ether extract was combined with the neutral organic solution and acidified to pH 2. The acid solution was extracted three times with dichloromethane. The extracts were combined, washed with saturated sodium chloride, dried and concentrated in vacuo. A portion of this residue was purified by preparative silica gel TLC, eluting with 1% methanol in dichloromethane. The resulting oil was crystallized from methylcyclohexane:diisopropyl ether (9:1), giving the desired product as yellow crystals, mp 74°–75° C. Proton nuclear magnetic resonance ($\delta$[ppm], CDCl$_3$) 90 MHz: 3.79 (s, 3H, OCH$_3$); 4.30 (s, 2H, CH$_2$CS); [7.00 (m, 2H) and 7.30 (m, 1H) (aromatic H's)]8.65 (bs, 1H, NH); 9.72 (bs, 1H, NH).

The non-alkaline soluble organic component was recovered and crystallized from diisopropyl ether, giving yellow crystals, mp 119.5°–121.5° C., of methyl [1-(methylthio)-2-(2-thienyl)ethylidene]hydrazinocarboxylate (Z isomer). Proton nuclear magnetic resonance ($\delta$[ppm], CDCl$_3$) 90 MHz: 2.45 (s, 3H); 3.75 (s, 3H); 3.85 (s, 2H); [6.98 (m, 2H) and 7.25 (m, 1H) (aromatic H's)]; 7.25 (bs, 1H).

EXAMPLE 11

2-[2-(4-Chlorophenyl)-1-thioxoethyl]hydrazinecarboxylic acid, methyl ester

A mixture of 200 g of 4-chlorophenyl acetic acid, 178.5 g of thionyl chloride and 600 ml of benzene was heated at reflux for 6 hours and then concentrated in vacuo. The residue was vacuum distilled, giving 215.8 g of 4-chlorophenyl acetyl chloride, bp 94°–95° C. (2.5 mmHg).

A solution of 120 g of dry pyridine, 103.2 g of piperidine and 1.5 liters of dry ether was stirred vigorously as 215.7 g of freshly distilled 4-chlorophenyl acetyl chloride in 250 ml of ether was added dropwise. After 4 hours the mixture was diluted with one liter of water and the organic phase collected. The aqueous phase was extracted with ether and the ether phases were combined, washed successively with 0.1N hydrochloric acid twice, 5% sodium hydroxide twice, saturated sodium chloride twice, dried and concentrated in vacuo. The residual oil was taken up in dichloromethane and percolated through a bed of neutral alumina with additional solvent. The resulting oil was crystallized from carbon tetrachloride:hexane (1:9), giving 243 g of N-(4-chlorophenylacetyl)piperidine as yellow crystals, mp 85°–85.5° C. A mixture of 200 g of N-(4-chlorophenylacetyl)piperidine, 94 g of phosphorous pentasulfide and 750 ml of pyridine was heated at reflux with vigorous stirring for 18 hours, then cooled and concentrated in vacuo. The residue was taken up in 1.8 liters of water, heated at 50° C. for 30 minutes, cooled and exhaustively extracted with ether. The ether extracts were combined, washed successively with water, 5% hydrochloric acid twice and saturated sodium chloride and dried. The solution was percolated through a bed of neutral alumina followed by elution with ether. The resulting oil was crystallized twice from methylcyclohexane, giving 100 g of N-(4-chlorophenylthioacetyl)piperidine as orange crystals, mp 82.5°–83.5° C.

A mixture of 200 g of N-(4-chlorophenylthioacetyl)piperidine, 117.5 g of bromoacetic acid and 600 ml of benzene was stirred overnight, then diluted with anhydrous ether and stirred overnight. The solid was collected and dried in vacuo giving 241 g of 1-[1-[(carboxymethyl)thio]2-(4-chlorophenyl)ethylidene]-piperidinium bromide, mp 118°–120° C.

A suspension of 181 g of the above compound in one liter of ethanol was treated with gaseous hydrogen sulfide for 4 hours and then stored for 96 hours. The suspension was concentrated in vacuo, then taken up in one liter of anhydrous ether and filtered. The filtrate was washed with water and saturated sodium chloride, dried and concentrated in vacuo. The resulting oil was crystallized from methylcyclohexane, giving 122.9 g of 2-[2-(4-chlorophenyl)-1-thioxoethyl]thioglycolic acid, ethyl ester as yellow needles, mp 36.5°–37° C.

A mixture of 130 g of 2-[2-(4-chlorophenyl)-1-thioxoethyl]thioglycolic acid, ethyl ester, 45 g of methyl hydrazinocarboxylate and 500 ml of dichloromethane was heated at reflux for 4 hours, then concentrated in vacuo. The residue was taken up in 1.2 liters of ether and extracted with three 500 ml portions of 0.5N sodium hydroxide. The alkaline extracts were combined, washed with ether and acidified with 6N hydrochloric acid to pH 4. The solution was extracted three times with a mixture of ether and dichloromethane. The organic phases were combined and concentrated. The residual oil was concentrated at 70°–75° C. for one hour at 0.1 mmHg. The residue was crystallized from acetone-methylcyclohexane and then from toluene, giving the desired product as ivory colored crystals, mp 147.5°–148° C. Proton nuclear magnetic resonance ($\delta$[ppm], CDCl$_3$) 90 MHz: 3.80 (s, 3H, OCH$_3$); 4.03 (s, 2H, CH$_2$CS); 7.31 (bs, 4H, C$_6$H$_4$); 8.60 (bs, 1H, NH); 9.90 (bs, 1H, NH).

EXAMPLE 12

2-[2-(4-Fluorophenyl)-1-thioxoethyl]hydrazinecarboxylic acid, methyl ester

A well stirred mixture of 111.8 g of piperidine, 103 g of pyridine and one liter of anhydrous ether was treated dropwise with 220 g of freshly distilled 4-fluorophenyl acetyl chloride. This mixture was stirred overnight, then filtered and the filtrate washed successively with water twice, 0.1N sodium hydroxide twice, 0.1N hydrochloric acid twice, water and saturated sodium chloride, then dried in vacuo. The residue was distilled giving a yellow liquid which crystallized on standing, giving 245 g of N-(4-fluorophenylacetyl)piperidine.

A mixture of 210 g of the above compound, 104 g of phosphorous pentasulfide and 800 ml of pyridine was heated at reflux with stirring for 4 hours, then cooled and concentrated in vacuo. The residue was taken up in one liter of cold water, heated to 40° C. for 15 minutes, cooled and extracted three times with ether. The ether extracts were combined and filtered through a bed of neutral alumina. The filtrate was evaporated in vacuo and the residual liquid vacuum distilled. The distillate was crystallized from toluene-ether, giving 165 g of N-(4-fluorophenylthioacetyl)piperidine, mp 65.5°–67.5° C.

A mixture of 118.6 g of the above compound, 76.2 g of bromoacetic acid and 600 ml of benzene was stirred for 24 hours, then 2 liters of ether was added. The suspension was stirred overnight and the solid collected, giving 150.2 g of 1-[1-[(carboxymethyl)thio]-2-(4-fluorophenyl)ethylidene]piperidinium bromide, mp 118°–119.5° C.

The above compound was reacted with hydrogen sulfide in ethanol as described in Example 11, giving 2-[2-(4-fluorophenyl)-1-thioxoethyl]thioglycolic acid, ethyl ester.

A mixture of 91.5 g of the above compound, 36 g of methyl hydrazinocarboxylate and 400 ml of dichloromethane was refluxed for 4 hours, then washed twice with water, once with saturated sodium chloride, dried and evaporated in vacuo. The residue was concentrated under high vacuum and recrystallized from toluene, giving 43 g of the desired product as ivory crystals, mp 149.5°–151.5° C. Proton nuclear magnetic resonance δ[ppm], CDCl$_3$ 90 MHz: 3.77 (s, 3H, OCH$_3$); 3.85 (s, 3H, OCH$_3$); 3.87 [s, 6H, OCH$_3$)(2X)]; 4.04 (s, 2H, CH$_2$CS); 6.52 (s, 2H, C$_6$H$_2$); 8.51 (bs, 1H, NH); 9.15 (bs, 1H, NH).

EXAMPLE 13

2-[2-(3-Methoxyphenyl)-1-thioxoet]hylhydrazine carboxylic acid methyl ester

A 200 g portion of 3-methoxyacetophenone was added dropwise with stirring over a one hour period to a mixture of 181 g of piperidine and 68.2 g of sulfur. This mixture was heated at 130° C. overnight, then concentrated in vacuo. The resulting oil was partitioned between dichloromethane and water. The aqueous layer was separated and extracted twice with dichloromethane. All organic phases were combined, washed with 5% hydrochloric acid, then twice with water and finally with saturated sodium chloride. The solution was filtered through a neutral alumina pad, the filtrate concentrated in vacuo and the residue slurried in 600 ml of ether and stored in a chill room. The solid was collected and dried in vacuo, giving 56 g of 1-[2-(3-methoxyphenyl)-1-thioxoethyl]piperidine as yellow crystals, mp 55°–56° C.

A mixture of 49.8 g of the above compound, 30.6 g of bromoacetic acid and 600 ml of toluene was stirred overnight and then diluted with 1.2 liters of ether. The solid was collected, washed with ether and dried in vacuo, giving 36.4 g of 1-[1-[(carboxymethyl)thio]-2-(3-methoxyphenyl)ethylidene]piperidinium bromide, mp 149°–151° C.

A 51 g portion of 1-[1-(carboxymethyl)thio]-2-(3-methoxyphenyl)ethylidene]piperidinium bromide wa slurried in 450 ml of isopropanol. Gaseous hydrogen sulfide was bubbled in for 4.5 hours, then the mixture was allowed to stand 48 hours and concentrated in vacuo. The residue was slurried in 200 ml of ether and filtered. The filter cake was washed three times with ether. The filtrate and washings were combined, concentrated in vacuo, the residue dissolved in 250 ml of ether and extracted with two 300 ml portions of 0.3N sodium hydroxide. The alkaline extracts were combined, acidified, extracted into dichloromethane, dried and concentrated in vacuo, giving 22 g of [[2-(3-methoxyphenyl)-1-thioxoethyl]thio]acetic acid, mp 93°–95° C.

A 20 g portion of the above compound was slurried in 80 ml of 1N sodium hydroxide, 10.5 g of methyl hydrazinocarboxylate was added followed by 100 ml of methanol. This mixture was stirred for 4 hours, poured into 100 ml of water, the pH adjusted to 4.5 and the mixture extracted three times with dichloromethane. The extracts were combined, washed with water, then saturated sodium chloride, dried and filtered through a bed of hydrous magnesium silicate. The filtrate was concentrated to an oil which was crystallized from cyclohexane, giving the desired product as ivory colored crystals, mp 56°–58° C. Proton nuclear magnetic resonance δ[ppm], CDCl$_3$ 90 MHz: 3.78 (s, 3H, OCH$_3$); 3.82 (s, 3H, OCH$_3$); 4.04 (s, 2H, CH$_2$CS); [6.90 (m, 3H) and 7.30 (dd, 1H, J =8.0 Hz; 8.0 Hz)(C$_6$H$_4$)]; 8.65 (bs, 1H, NH); 9.80 (bs, 1H, NH).

EXAMPLE 14

2-[1-Thioxo-2-[3-(trifluoromethyl)phenyl]ethyl]hydrazinecarboxylic acid, methyl ester A suspension of 95 g of 3-(trifluoromethyl)phenylacetic acid in 500 ml of dry benzene was treated with 71.4 g of thionyl chloride. After refluxing for 4 hours the solvent was removed in vacuo and the residue azeotroped twice with toluene. A solution of this material in 250 ml of ether was used to treat a cold solution of 85 g of piperidine in 400 ml of ether. After 2 hours the reaction was diluted with 600 ml of water and extracted three times with ether. The extracts were combined, washed twice with saturated sodium chloride, dried and concentrated in vacuo. The resulting oil was vacuum distilled giving an oil, bp 136°–138° C. (0.9 mmHg) which was crystallized from heptane giving 93 g of 1-[[3-(trifluoromethyl)phenyl]acetyl]piperidine, mp 34.5°–35.5° C.

A mixture of 135.6 g of 1-[[3-(trifluoromethyl)phenyl]acetyl]piperidine, 101.1 g of Lawesson's reagent and 400 ml of benzene was heated at reflux for 6 hours, cooled and concentrated in vacuo. The residue was taken up in dichloromethane, filtered through a bed of neutral alumina with 3 liters of dichloromethane elution. The filtrate was concentrated in vacuo. The resulting oil was vacuum distilled giving 131 g of 1-[1-thioxo-2-[3-(trifluoromethyl)phenyl]ethyl]piperidine, bp 181°–182° C. (3.0 mmHg).

A solution of 125 g of the above compound in 400 ml of benzene was treated with 75.2 g of ethyl bromoacetate. After standing 2 hours, the mixture was diluted with 500 ml of dry ether and filtered. The filter cake was washed with dry ether and dried in vacuo, giving 150 g of 1-[1-[(2-ethoxy-2-oxoethyl)thio]-2-[3-(trifluoromethyl)phenyl]ethylidene]piperidinium bromide as a white solid, mp 129°–132° C.

A suspension of 145 g of the above compound in 500 ml of dry ethanol was treated with gaseous hydrogen sulfide for 40 minutes, then stored overnight and concentrated in vacuo. The residue was suspended in 700 ml of ether and filtered. The filtrate was washed with ether until all yellow color was absent, then concentrated in vacuo and vacuum distilled, giving 80 g of [[1-thioxo-2-[3-(trifluoromethyl)phenyl]ethyl]thio]acetic acid, ethyl ester, bp 177°–178° C. (5.0–5.5 mmHg).

A solution of 64.5 g of the above compound, 22.5 g of methyl hydrazinocarboxylate and 400 ml of dichloromethane was heated at reflux for 4 hours, cooled and then diluted with 600 ml of dichloromethane. The solution was washed with water (thrice), and saturated sodium chloride (twice), dried and concentrated in vacuo. The residue was taken up in dichloromethane, filtered through a bed of hydrous magnesium silicate with additional solvent and the filtrate evaporated. The solid was crystallized from toluene, giving 6 g of the desired product as yellow crystals, mp 131°–132.5° C. Proton nuclear magnetic resonance (δppm], CDCl$_3$) 90 MHz: 3.80 (s, 3H, OCH$_3$); 4.10 (s, 2H, CH$_2$CS); 7.55 (m, 4H, C$_6$H$_4$); 8.55 (bs, 1H, NH); 9.90 (bs, 1H, NH).

EXAMPLE 15

2-(3-Ethoxy-3-oxo-1-thioxopropyl)hydrazinecarboxylic acid, methyl ester

A mixture of 1-[(ethoxycarbonyl)acetyl]piperidine, 131 g of phosphorus pentasulfide and one liter of toluene was stirred for 96 hours. The solvent was decanted and saved. The gum was washed with 250 ml of toluene. The toluene solutions were combined and concentrated in vacuo. The residue was dissolved in dichloromethane and percolated through a bed of hydrous magnesium silicate, washing with the same solvent. The filtrate and wash were combined and concentrated in vacuo, giving 92 g of ethyl 3-thioxo-N-piperidinepropionate.

A solution of 92 g of the above compound, 65.5 g of methyl bromoacetate and 300 ml of benzene was stirred for 96 hours. The resulting crystals were collected, washed with cold benzene and dried in vacuo, giving 115 g of 1-[1-(2-methoxy-2-oxoethyl)thio]-2-[(ethoxycarbonyl)ethylidene]piperidinium bromide, mp 92°–94° C.

A mixture of 110 g of the above compound and 500 ml of methanol was treated with gaseous hydrogen sulfide until 1.2 equivalents were taken up. The mixture was kept overnight and then concentrated in vacuo. The residue was taken up in ether, filtered, washed with ether and the filtrate and wash combined, concentrated in vacuo and vacuum distilled, giving [1-thioxo-2-[(ethoxycarbonyl)ethyl]thio]acetic acid, methyl ester as a liquid, bp 136°–138° C., (4 mmHg).

A mixture of 49 g of the above compound, 19.9 g of methyl hydrazinocarboxylate and 400 ml of dichloromethane was heated at reflux for 5 hours, then washed with water, saturated sodium chloride, dried and concentrated in vacuo to an oil. The oil was further concentrated at high vacuum. The residue was taken up in dichloromethane and chromatographed on a column of silica gel packed in the same solvent. The column was eluted with 2 liters of dichloromethane and then 2 liters of ether. The desired fractions were combined and worked up, giving 30 g of the desired compound as a yellow oil. Proton nuclear magnetic resonance δ[ppm], CDCl$_3$) 90 MHz: 1.30 (t, 3H, CH$_3$CH$_2$O); 3.87 (s, 3H, OCH$_3$); 3.91 (s, 3H, CH$_2$CS); 4.27 (q, 2H, OCH$_2$CH$_3$); 8.85 (bs, 1H, NH); 11.52 (bs, 1H, NH).

EXAMPLE 16

2-[2-(Phenylthio)-1-thioxoethyl]hydrazinecarboxylic acid, methyl ester

A suspension of 168.5 g of thiophenoxyacetic acid, 750 ml of benzene and 142.7 g of thionyl chloride was heated at reflux for 10 hours, then concentrated in vacuo. The residue was taken up in 500 ml of dry ether and added dropwise to a cold, stirred solution of 189.2 g of pyridine in 1.7 liters of dry ether. After 6 hours, water was added and the two phases separated. The aqueous phase was extracted twice with ether, all organic phases were combined, washed successively with 5% sodium hydroxide twice, water, 1N hydrochloric acid twice, water and saturated sodium chloride, then dried and concentrated in vacuo. The residue was crystallized from methylcyclohexane, giving 211 g of 2-[2-(phenylthio)acetyl]piperidine, mp 68.5°–69.5° C.

A mixture of 117.6 g of the above compound, 102 g of Lawesson's reagent and 750 ml of toluene was heated at 80° C. for 12 hours, then cooled, percolated through a bed of hydrous magnesium silicate and eluted with dichloromethane. The filtrate was concentrated in vacuo giving an oil which was crystallized from cyclohexane, giving 115 g of 1-[1-thioxo-2-[2-(phenylthio)]ethyl]piperidine, mp 83°–84° C.

A solution of 110 g of the above compound, 67 g of methyl bromoacetate and 450 ml of benzene was stirred overnight, then filtered. The filter cake was washed with cold 2-butanone until ivory colored, then dried in vacuo, giving 165 g of 1-[1-[(2-methoxy-2-oxoethyl)thio]-2-[(phenylthio)methyl]ethylidene]piperidinium bromide, mp 165°–70° C.

A mixture of 160 g of the above compound and 600 ml of dry methanol was treated for 4 hours with gaseous hydrogen sulfide, then stored overnight and the solvent removed in vacuo. The residue was taken up in 400 ml of ether and filtered. The filter cake was washed with ether until colorless. The filtrate and washings were combined, concentrated in vacuo, taken up in dichloromethane and filtered through a bed of hydrous magnesium silicate with dichloromethane elution. Evaporation gave [1-thioxo-2-[2-(phenylthio)ethyl]thio]acetic acid, methyl ester as a liquid.

A mixture of 91 g of the above compound, 36 g of methyl hydrazinocarboxylate and 300 ml of dichloromethane was heated at reflux for 3 hours and then diluted with 600 ml of ether. This solution was extracted three times with saturated sodium carbonate. The alkaline extracts were combined, washed with ether, acidified to pH 2 and extracted twice with dichloromethane. The organic extracts were combined, washed with water and saturated sodium chloride, dried and concentrated in vacuo, giving an oil. This oil was dissolved in dichloromethane, percolated through a bed of hydrous magnesium silicate with the same solvent and evaporated, giving 50.2 g of the desired compound as a yellow oil. Proton nuclear magnetic resonance δ[ppm], CDCl$_3$) 90 MHz: 3.79 (s, 3H, OCH$_3$); 4.18 (s, 2H, SCH$_2$CS); 7.32 (bs, 5H, C$_6$H$_5$); 8.55 (bs, 1H, NH); 10.55 (bs, 1H, NH).

EXAMPLE 17

2-[2-(Tetrahydro-2H-pyran-2-yl)-1-thioxoethyl]hydrazinecarboxylic acid, methyl ester 2-[2-(Tetrahydro-2H-pyran-2-yl)]acetic acid was reacted as described in Example 16, giving 2-[2-[(tetrahydro-2H-pyran-2-yl)-1-thioxo]thio]acetic acid, ethyl ester.

A mixture of 78.7 g of the above compound, 29.3 g of methyl hydrazinocarboxylate and 400 ml of dichloromethane was stirred overnight, then evaporated in vacuo. The residue was taken up in 250 ml of dichloromethane and percolated through a bed of magnesium trisilicate with the same solvent. The filtrate was concentrated in vacuo, then under high vacuum (0.2 mm Hg), giving an oil. This oil was crystallized from diisopropyl ether at 0° C., giving 64.5 g of the desired product as ivory colored crystals, mp 109.5°–110.5° C. Proton nuclear magnetic resonance δ[ppm], CDCl$_3$) 300 MHz: 1.35–1.85 [m, 6H, (CH$_2$)$_3$CH$_2$O]; 2.92 (m, 2H, CHCH$_2$CS); 3.55 (m, 2H, CH$_2$O); 3.79 (s, 3H, OCH$_3$); 4.10 (m, 1H, CHCH$_2$); 8.72 (bs, 1H, NH); 10.98 (bs, 1H, NH).

EXAMPLE 18

2-(Aminocarbonyl)hydrazide benzenepropanethioic acid

Phenylthiopropionylpiperidine was converted to [(3-phenyl-1-thioxopropyl)thio]acetic acid, ethyl ester by the general procedure of Example 16, using ethyl bromoacetate.

A solution of 50 g of the above compound in 400 ml of ethanol was treated with a solution of 25.1 g of semicarbazide hydrochloride and 18.5 g of anhydrous sodium acetate in 150 ml of water. After 2 hours the mixture was concentrated in vacuo, the residue taken up in 400 ml of toluene and stored at 5° C. for 12 hours. The solid was collected, washed with toluene and dried in vacuo, giving 35 g of the desired compound as white crystals, mp 118°–119° C. Proton nuclear magnetic resonance δ[ppm], CDCl$_3$) 90 MHz: 2.95 (m, 2H, CH$_2$); 3.12 (m, 2H, CH$_2$); 4.79 (bs, 2H, NH$_2$); 7.28 (bs, 5H, C$_6$H$_5$); 8.83 (bs, 1H, NH); 9.75 (bs, 1H, NH).

EXAMPLE 19

2-(Aminocarbonyl)hydrazide propanethioic acid

A solution of thiopropionylpiperidine in 700 ml of dry ether was treated with ethyl bromoacetate. The mixture was stored for 26 hours, then the solid was collected, washed with ether and dried in vacuo. This solid was dissolved in 1100 ml of anhydrous ethanol and treated with gaseous hydrogen sulfide. After 12 hours the mixture was concentrated in vacuo, the suspension taken up in one liter of ether and filtered. The filter cake was washed with ether until no yellow color remained. The filtrate and wash were combined and concentrated in vacuo, giving a liquid which was distilled, giving [(1-thioxopropyl)thio]acetic acid, ethyl ester as a light orange oil, bp 105°–107° C. (2 mmHg).

A solution of 78.1 g of semicarbazide hydrochloride in 500 ml of ethanol was treated with 57.4 g of anhydrous sodium acetate. After 30 minutes a solution of 118.2 g of the above compound was added, the reaction was heated at 70°–75° C. for 4 hours and then concentrated in vacuo. The residue was suspended in 800 ml of dichloromethane, stirred vigorously for 10 minutes and the solvent decanted. The gum was taken up in 500 ml of ethyl acetate and 1500 ml of ethanol and filtered. The filtrate was concentrated in vacuo. The filter cake was boiled three times with 700 ml portions of ethanol. These extracts were combined with the above concentrate and evaporated. The residue was crystallized from ethanol-ethyl acetate, giving 46 g of the desired compound as white crystals, mp 136°–137° C. Proton nuclear magnetic resonance δ[ppm], CDCl$_3$) 90 MHz: 1.20 (t, 3H, CH$_3$); 2.60 (q, 2H, CH$_2$CS); 5.70 (bs, 2H, NH$_2$); 9.33 (bs, 1H, NH); 11.33 (bs, 1H, NH).

EXAMPLE 20

2-(Aminocarbonyl)hydrazide butanethioic acid

[(1-Thioxobutyl)thio]acetic acid, ethyl ester was prepared by the procedure of Example 19, using 1-thiobutylpiperidine.

A mixture of 250 g of semicarbazide hydrochloride, anhydrous sodium acetate, 250 g of the above compound and 1.2 liters of water was stirred overnight and then concentrated in vacuo. The resdue was taken up in 900 ml of water and extracted three times with ethyl acetate. The extracts were combined, washed with water twice, then saturated sodium chloride, dried and concentrated in vacuo. The residue was crystallized from ethyl acetate-t-butyl methyl ether, giving 150.6 g of the desired compound as white crystals, mp 134.5°–136° C. Proton nuclear magnetic resonance δ[ppm], CDCl$_3$) 90 MHz: 0.95 (t, 3H, CH$_3$); 1.80 (m, 2H, CH$_2$CH$_3$); 2.64 (t, 2H, CH$_2$CS); 5.85 (bs, 2H, NH$_2$); 9.27 (bs, 1H, NH); 11.27 (bs, 1H, NH).

EXAMPLE 21

3-(1,2,3-Thiadiazol-4-ylthio)propanoic acid, methyl ester

A 4.6 g portion of ethyl carbazate was carefully added to 50 ml of acetic anhydride producing an exotherm. The reaction was heated on a steam bath for one hour, then evaporated to an oil. The oil was crystallized from chloroform giving acetyl carbazate ethyl ester.

The above compound was reacted with phosphorous pentachloride on a steam bath, then evaporated to an oil which was crystallized from chloroform.

To a cold solution of the above compound in tetrahydrofuran was added a cold solution of the sodium salt of 3-mercaptopropionic acid, methyl ester in methanol. After standing at room temperature for several hours the mixture was filtered. The filtrate was evaporated to dryness, the residue dissolved in ethyl acetate, filtered and the filtrate evaporated to an oil. This oil was added to 25 ml of thionyl chloride, allowed to stand ½ hour and then evaporated to dryness. The residue was evaporated twice from dichloromethane, then dissolved in ethyl acetate and washed with saturated sodium bicarbonate, water and brine, then dried and evaporated to dryness. The residue was chromatographed on 600 ml of silica gel, eluting with ethyl acetate:hexane (1:2), collecting 200 ml fractions. The third fraction was then chromatographed on preparative silica gel plates eluting with acetone, giving 841 mg of the desired compound as a light orange oil. Proton nuclear magnetic resonance (δ[ppm], CDCl$_3$) 90 MHz: 2.76 (t, 2H, J=6.5 Hz, CH$_2$CO$_2$); 3.48 (t,2H, SCH$_2$); 3.71 (s, 3H, CH$_3$O); 8.33 (s, 1H, H-5).

EXAMPLE 22

3-(1,2,3-Thiadiazol-4-ylthio)propanoic acid, ethyl ester

One mole of methyl magnesium bromide in ether was diluted with one liter of dry tetrahydrofuran. The ether was removed by distillation and the tetrahydrofuran solution kept at 45° C. as 80 g of carbon disulfide was added dropwise. When addition was complete the mixture was heated at 50°–55° C. for one hour, then 140 g of ethyl 3-bromopropionate was added dropwise. The reaction was then heated at reflux for 4 hours, cooled overnight and diluted with one liter of water. The mixture was washed successively with ether (thrice), water (twice) and saturated sodium chloride, then dried and evaporated. The residual liquid was vacuum distilled, giving 70 g of ethyl 3-[(1-thioxoethyl)thio]propionate as a yellowishg orange liquid, bp 82°-84° C. (0.5 mmHg).

A mixture of 9 g of the above compound, 12.5 g of methyl hydrazinocarboxylate and 300 ml of chloroform was heated at reflux for 3 hours, cooled and concentrated in vacuo. The oily residue was then concentrated at 70° C., 2 mm Hg for one hour, then dissolved in 400 ml of ether and washed twice with water. The organic phase was dried and concentrated in vacuo, giving 2-(1-thioxoethyl)hydrazinecarboxylic acid, methyl ester as a viscous orange oil.

A mixture of 29.6 g of the above compound, 50 ml of ethyl acrylate, 5 ml of triethylamine, and 300 ml of benzene was heated at reflux for 12 hours and concentrated in vacuo. The crude oil was chromatographed over hydrated magnesium trisilicate with dichloromethane and the desired fractions pooled. The yellow oil was crystallized from diisopropyl ether to yield 45.0 g of (Z)-[1-[(3-ethoxy-3-oxopropyl)thio]ethylidene]hydrazinecarboxylic acid, methyl ester.

A mixture of 2.5 g of the above compound, 20 ml of thionyl chloride and 10 ml of dry dichloromethane was heated at reflux for 3 hours, then concentrated in vacuo. The residual oil was taken up in dichloromethane and filtered through a bed of hydrous magnesium silicate with the same solvent. The resulting oil was purified by preparative TLC on silica gel, eluting with dichloromethane, giving 907 mg of the desired compound as a yellowish orange oil. Proton nuclear magnetic resonance ($\delta$[ppm], CDCl$_3$) 90 MHz: 1.28 (t, 3H, J=7.0 Hz, CH$_3$); 2.79 (t, 2H, J=6.5 Hz, CH$_2$CO$_2$); 3.48 (t, 2H, SCH$_2$); 4.16 (q, 2H, OCH$_2$); 8.35 (s, 1H, 5-H). Infrared spectrum (neat): 3120 (m); 1740(s); 1260–1125(s); 948–885.

EXAMPLE 23

3-[(5-Methyl-1,2,3-Thiadiazol-4-Vl)thio]propanoic Acid, Ethyl Ester

A suspension of 73.6 g of 2-(aminocarbonyl)hydrazide propanethioic acid in 750 ml of dry acetone was treated with 69.3 g of anhydrous potassium carbonate. After stirring for 30 minutes, 14.2 g of freshly prepared ethyl 3-iodopropionate was added, then the mixture was heated at reflux, cooled and concentrated to ½ volume. One liter of water was added and the mixture was extracted twice with dichloromethane. The extracts were combined, washed with water, 5% sodium chloride, dried and evaporated in vacuo. The residual oil was purified by chromatography on silica gel. The oil was applied with dichloromethane and eluted with the same solvent. The solvent system was then changed to a 2-5% gradient of methanol in dichloromethane. The active fractions were combined, concentrated to an oil and crystallized from diisopropyl ether, giving 3-[[1-[(aminocarbonyl)hydrazono]propyl]thio]propanoic acid, ethyl ester as white needles, mp 63.5°–64.5° C..

A solution of 49.4 g of the above compound was reacted with thionyl chloride as described in Example 22, giving the desired compound as a light yellow oil. Proton nuclear magnetic resonance ($\delta$[ppm], CDCl$_3$) 90 MHz: 1.26 (t, 3H, J=7.0 Hz, CH$_3$CH$_2$); 2.55 (s, 3H, CH$_3$); 2.70 (t, 2H, J=7.0 Hz, CH$_2$CO); 3.39 (t, 2H, SCH$_2$); 4.14 (q, 2H, OCH$_2$CH$_3$). Infrared absorption spectrum (neat): 1735(s); 1460(w); 1420(w); 1370(m); 1342(m); 1285(m); 1245(m); 1218(m); 1170(m); 1140(m); 1045(m); 1040(m); 1025(m); 1010(m); 890(m).

EXAMPLE 24

3-[(5-ethyl-1,2,3-thiadiazol-4-yl)thio]propanoic acid, ethyl ester

3-[[1-[(Aminocarbonyl)hydrazono]butyl]thio]propanoic acid, ethyl ester was prepared from 2-(aminocarbonyl)hydrazide butanethioic acid as described in Example 23.

A 130.7 g portion of the above compound was reacted with thionyl chloride as described in Example 22, giving 83 g of the desired compound as a light yellow oil. Proton nuclear magnetic resonance ($\delta$[ppm], CDCl$_3$) 90 MHz: 1.27 (t, 3H, J=7.2 Hz, CH$_3$CH$_2$O); 1.36 (t, 3H, J=7.0 Hz, CH$_3$CH$_2$); 2.73 (t, 2H, CH$_2$CO); 2.96 (q, 2H, CH$_2$C=); 3.43 (t, 2H, SCH$_2$). Infrared absorption spectrum (neat): 1735(s); 1460(w); 1415(w); 1370(m); 1342(w); 1285(w); 1245(w); 1220(w); 1170(m); 1140(m); 1045(m); 1025(m); 1011 (m); 890(m).

EXAMPLE 25

3-[[5-(1,1-Dimethylethyl)-1,2,3-thiadiazol-4-yl]thio]propanoic acid, methyl ester A mixture of 20.5 g of 2-(3,3-dimethyl-1-thioxobutyl)-hydrazinecarboxylic acid, methyl ester, 12.92 g of methyl acrylate, 1 ml of triethylamine and 300 ml of dry benzene was heated at reflux for 8 hours, then cooled and concentrated in vacuo. The residual oil was chromatographed through a bed of hydrous magnesium silicate, eluting with dichloromethane and evaporated, giving 27 g of (Z)-[1-[(3-methoxy-3-oxopropyl)thio]-3,3-dimethylbutylidene]hydrazinecarboxylic acid, methyl ester.

A solution of 29 g of the above compound, 17.9 g of thionyl chloride and 300 ml of benzene was heated at reflux for 18 hours, then cooled and concentrated in vacuo. The oily residue was taken up in 500-600 ml of ether, washed with 2% sodium hydroxide twice, water and saturated sodium chloride, dried and concentrated in vacuo. The residue was dissolved in benzene, applied to a column of silica gel packed in petroleum ether and eluted with 1.5 liters of benzene, followed by 1.5 liters of 5% ethyl acetate in petroleum ether. The desired fractions were combined and evaporated, giving 17.5 g of the desired compound as a light orange oil. Proton nuclear magnetic resonance ($\delta$[ppm], CDCl$_3$) 90 MHz: 1.51 (s, 9H, t-butyl); 2.85 (t, 2H, J=6.5 Hz, CH$_2$CO); 3.60 (t, 2H, SCH$_2$); 3.70 (s, 3H, OCH$_3$). Infrared absorption spectrum (neat): 1735(s); 1460(m); 1430(m); 1400(m); 1355(m); 1245(m); 1210(m); 1170(m); 1150(m); 925(m).

EXAMPLE 26

3-[[5-(1,1-Dimethylethyl)-1,2,3-thiadiazol-4-yl]thio]propanoic acid, ethyl ester A mixture of [1-[(3-ethoxy-3-oxopropyl)thio]-3,3-dimethylbutylidene]hydrazinecarboxylic acid, methyl ester, thionyl chloride and dichloromethane was heated at reflux for 40 hours and then quenched with ice water. The orange product was extracted twice into ether. The extracts were combined, washed with 0.1N sodium hydroxide twice, water twice, saturated sodium chloride twice, dried and concentrated in vacuo. The resulting orange liquid was evaporated onto 70 g of silica gel.

The gel was dried and poured onto a column of silica gel packed in petroleum ether. The column was eluted with a gradient of 1–10% ethyl acetate in petroleum ether. The desired fractions were purified on silica gel preparative TLC plates eluting with 3% ethyl acetate in petroleum ether, giving 2.9 g of the desired compound as a light yellow oil. Proton nuclear magnetic resonance (δ[ppm], CDCl$_3$) 90 MHz: 1.23 (t, 3H, J=7.0 Hz, CH$_3$); 1.49 (s, 9H, t-butyl); 2.84 (t, 2H, J=7.0 Hz, CH$_2$CO); 3.59 (t, 2H, SCH$_2$); 4.14 (q, 2H, OCH$_2$).

EXAMPLE 27

3-[(5-phenyl-1,2,3-thiadiazol-4-yl)thio]propanoic acid, ethyl ester

[1-[(3-Ethoxy-3-oxopropyl)thio]-2-(phenyl)ethylidene]hydrazinecarboxylic acid, methyl ester was prepared from 2-(2-phenyl-1-thioxoethyl)hydrazinecarboxylic acid, methyl ester.

A mixture of 16.2 g of the above compound, 23.6 g of thionyl chloride and 100 ml of dry dichloromethane was heated at reflux for 3 hours and then concentrated in vacuo. The residue was taken up in a mixture of ether and dichloromethane, washed three times with water, then saturated sodium chloride, dried and concentrated to an oil. This oil was purified on a silica gel column, eluting with dichloromethane. The desired fractions were combined and worked up giving 12.5 g of the desired compound as white cubes, mp 57.5°–58.5° C. Proton nuclear magnetic resonance (δ[ppm], CDCl$_3$) 90 MHz: 1.22 (t, 3H, J=7.0 Hz, CH$_3$); 2.76 (t, 2H, J=6.5 Hz, CH$_2$CO); 3.52 (t, 2H, SCH$_2$); 4.08 (q, 2H, OCH$_2$); 7.53 (bs, 5H, C$_6$H$_5$). Infrared absorption spectrum (KBr pellet): 1740(s); 1225(s); 1195(s); 1175(s); 1155(s); 1015(s); 932(s); 758(s); 685–690(s).

EXAMPLE 28

3-[[5-(4-methylphenyl)-1,2,3-thiadiazol-4-yl]thio]-propanoic acid, ethyl ester

A mixture of 30 g of 2-[2-(4-methylphenyl)-1-thioxoethyl]hydrazinecarboxylic acid, methyl ester, 25 g of ethyl acrylate, 500 μl of triethylamine and 250 ml of benzene was heated at reflux for 24 hours, cooled and concentrated in vacuo. The resulting oil was purified by dry column chromatography on silica gel, eluting with dichloromethane. The desired fractions were collected and evaporated, giving [1-[(3-ethoxy-3-oxopropyl)thio]-2-(4-methylphenyl)ethylidene]hydrazinecarboxylic acid, methyl ester as an oil.

A solution of 28 g of the above compound, 23.8 g of thionyl chloride and 125 ml of dry dichloromethane was heated at reflux for 5 hours, then poured into ice. This mixture was extracted three times with ether. The extracts were combined, washed successively with water twice, 5% aqueous sodium bicarbonate twice, water and saturated sodium chloride, dried and evaporated. The resulting oil was purified on a silica gel dry column, eluting with dichloromethane. The active fraction was concentrated under high vacuum, giving an oil. This oil was crystallized from methylcyclohexane at 20° C., giving the desired product as ivory colored needles, mp 68.5°–69.5° C. Proton nuclear magnetic resonance (δ[ppm], CDCl$_3$) 90 MHz: 1.22 (t, 3H, J=7.0 Hz, CH$_3$); 2.42 (s, 3H, CH$_3$C$_6$H$_4$); 2.80 (t, 2H, J=7.5 Hz, CH$_2$CO$_2$); 3.58 (t, 2H, SCH$_2$); 4.15 (q, 2H, OCH$_2$); [7.27 (d, 2H, J=8.0 Hz) and 7.50 (d, 2H)(C$_6$H$_4$)]. Infrared absorption spectrum (KBr pellet): 1735(s); 1518(w); 1480(w); 1460(w); 1440(w); 1412(w); 1400(w); 1365(w); 1230(m); 1200(s); 1160(m); 1021(m); 935(m); 820(m).

EXAMPLE 29

3-[[5-[4-(1,1-Dimethylethyl)phenyl]-1,2,3-thiadiazol-4-yl]thio]propanoic acid, ethyl ester A mixture of 35 g of 2-[2-[4-(1,1-dimethylethyl)phenyl]-1-thioxoethyl]hydrazinecarboxylic acid, methyl ester, 20.2 g of ethyl acrylate, 1.0 ml of triethylamine and 250 ml of benzene was heated as reflux for 28 hours and then concentrated in vacuo. The resulting oil was purified over a dry column of silica gel, eluting with dichloromethane. The active fractions were combined and evaporated giving 45.2 g of a 2/1 mixture of [Z(and E)]-[2-[4-(1,1-dimethylethyl)phenyl]-1-[(3-ethoxy-3-oxopropyl)thio]ethylidene]hydrazinecarboxylic acid methyl ester as a faint yellow oil.

A 40 g portion of the above mixture, 250 ml of dry dichloromethane and 26.9 g of thionyl chloride were mixed, heated at reflux for 3 hours and then poured into ice. The mixture was extracted three times with ether. The extracts were combined, washed twice with water, twice with 5% aqueous sodium bicarbonate, water and saturated sodium chloride, dried and evaporated. The resulting oil was purified by dry column chromatography on silica gel, eluting with dichloromethane. The desired fractions were pooled and concentrated, giving 27.6 g of the desired product as an orange oil. Proton nuclear magnetic resonance (δ[ppm], CDCl$_3$) 90 MHz: 1.24 (t, 3H, J=7.0 Hz, CH$_3$); 1.32 (s, 9H, t-butyl); 2.83 (t, 2H, J=6.5 Hz, CH$_2$CO$_2$); 3.60 (t, 2H, SCH$_3$); 4.15 (q, 2H, OCH$_3$); 7.55 (s, 4H, C$_6$H$_4$). Infrared absorption spectrum (neat): 1740(s); 1610(m); 1522(m); 1375(m); 1270(m); 1250(m); 1220(m); 1200(m); 1180(m); 935(s); 840(s).

EXAMPLE 30

3-[[5-(4-methoxyphenyl)-1,2,3-thiadiazol-4-yl]thio]-propanoic acid, ethyl ester

A mixture of 50.9 g of 2-[2-(4-methoxyphenyl)-thioxoethyl]hydrazinecarboxylic acid, methyl ester, 30 g of ethyl acrylate, 2 ml of triethylamine and 450 ml of benzene was heated at reflux for 27 hours, then cooled and concentrated in vacuo. The resulting oil was purified as described in Example 29, giving [Z(and E)]-[1-[(3-ethoxy-3-oxopropyl)thio]-2-(4-methoxyphenyl)ethylidene]hydrazinecarboxylic acid, methyl ester.

A 52.4 g portion of the above compound, 29.8 g of thionyl chloride and 300 ml of dichloromethane were mixed, stirred for 5 hours and then poured onto chipped ice. This mixture was extracted three times with ether. The extracts were combined, washed with water, twice with 1% sodium hydroxide, twice with water saturated sodium chloride, dried and evaporated. The resulting oil was purified on a dry column of silica gel, eluting with 1.5 liters of 10% ethyl acetate in hexane. The desired fraction was evaporated to an oil which was crystallized from diisopropyl ether at 0°–5° C., giving 25 g of the desired product as ivory colored needles, mp 50.5°–515° C. Proton nuclear magnetic resonance (δ[ppm], CDCl$_3$) 90 MHz: 1.21 (t, 3H, J=7.0 Hz, CH$_3$); 2.78 (t, 2H, J=7.0 Hz, CH$_2$CO); 3.51 (t, 2H, SCH$_2$); 3.85 (s, 3H, OCH$_3$); 4.12 (q, 2H, OCH$_2$); [6.99 (d, 2H, J=9.0 Hz) and 7.55 (d, 2H, (C$_6$H$_4$)]. Infrared absorption spectrum: 1735(s); 1615(m); 1520(m); 1480(m); 1465(w); 1445(w); 1418(w); 1400(w); 1370(w); 1355(w); 1265(m);

1225(m); 1205(m); 1180(m); 1155(m); 1035(m); 1018(m); 830–840(m).

EXAMPLE 31

3-[[5-(3,4,5-Trimethoxyphenyl)-1,2,3-thiadiazol-4yl]hio]propanoic acid, ethyl ester A mixture of 2-[1-thioxo-2-(3,4,5-trimethoxyphenyl)ethyl]hydrazinecarboxylic acid, methyl ester, ethyl acrylate, triethylamine and benzene was treated as described in Example 30, giving [Z(and E)]-[1-[(3-ethoxy-3-oxopropyl)thio]-2-(3,4,5-trimethoxyphenyl)ethylidene]hydrazinecarboxylic acid, methyl ester.

A 13.8 g portion of the above mixture was reacted as described in Example 30 and purified by chromatography, eluting with dichloromethane. The resulting oil was crystallized from diethyl ether, giving 5.6 g of the desired product as ivory needles, mp 27°–27.5° C. Proton nuclear magnetic resonance ($\delta$[ppm], CDCl$_3$) 90 MHz: 1.24 (t, 3H, J=7.0 Hz, CH$_3$); 2.82 (t, 2H, J=6.5 Hz, CH$_2$CO$_2$); 3.60 (t, 2H, SCH$_2$); 3.91 (s, 9H, OCH$_3$'s); 4.15 (q, 2H, OCH$_2$); 6.81 (s, 2H, C$_6$H$_2$). Infrared absorption spectrum (KBr pellet): 1735(s); 1580(s); 1515(s); 1470(s); 1415(s); 1330(s); 1250(s); 1180(m); 1130(s).

EXAMPLE 32

3-[[5-(2-Naphthyl)-1,2,3-thiadiazol-4-yl]thio propanoic acid, ethyl ester

A solution of 20 g of 2-[2-(2-naphthyl)-1-thioxoethyl]-hydrazinecarboxylic acid, methyl ester, 1 ml of triethylamine, 12 g of ethyl acrylate and 200 ml of toluene was heated at 80° C., then concentrated. The residue was taken up in 500 ml of dichloromethane, passed through hydrous magnesium silicate, treated with charcoal, filtered through sodium sulfate and concentrated in vacuo. The resulting oil was dissolved in 50 ml of toluene, stored in a chill room overnight and concentrated in vacuo to an oil. This oil was purified on a dry silica gel column, eluting with heptane:ethyl acetate (1:1). The desired fraction was collected, dissolved in dichloromethane, passed through an alumina pad and evaporated, giving [E(and Z)]-2-[1-[(3-ethoxy-3-oxopropyl)-thio]-2-(2-naphthyl)ethylidine]hydrazinecarboxylic acid, methyl ester.

A 13 g portion of the above mixture was dissolved in 80 ml of dichloromethane. A solution of 8.6 g of thionyl chloride in 40 ml of dichloromethane was added dropwise with stirring. The mixture was stirred 2.5 hours, then heated at 70° C. for 3 hours, allowed to stand overnight, poured onto 400 g of crushed ice and stirred for one hour. The aqueous layer was extracted twice with dichloromethane. All organic solutions were combined, washed with saturated sodium bicarbonate, water and saturated sodium chloride, dried, passed through a bed of neutral alumina and concentrated in vacuo to an oil. The oil was crystallized from diethyl ether, giving 3.6 g of the desired product as ivory crystals, mp 46.5°–47.5° C. Proton nuclear magnetic resonance ($\delta$[ppm], CDCl$_3$) 90 MHz: 1.23 (t, 3H, J=7.0 Hz, CH$_3$); 2.84 (t, 2H, J=7.0 Hz, CH$_2$CO$_2$); 3.60 (t, 2H, SCH$_2$); 4.13 (q, 2H, OCH$_2$); 7.45–8.25 (m, 7H, C$_{10}$H$_7$).

EXAMPLE 33

3-[[5-(2-Thienyl)-1,2,3-thiadiazol-4-yl]thio]propanoic acid, ethyl ester

A mixture of 45.6 g of 2-[(2-thienyl)-1-thioxoethyl]-hydrazinecarboxylic acid, methyl ester, 50.0 g of ethyl acrylate, 500 ml of benzene, and 5 ml of triethylamine was heated at reflux for 18 hours and concentrated in vacuo. The oily residue was taken up into dichloromethane and percolated through a bed of hydrated magnesium trisilicate with dichloromethane. The desired fractions of [Z(and E)]-[1-[(3-ethoxy-3-oxopropyl)thio]-2-(2-thienyl)ethylidene]hydrazinecarboxylic acid, methyl ester were pooled and concentrated to yield 54.7 g of yellow oil.

A mixture of 32.9 g of the above compound, 25 g of thionyl chloride, and 500 ml of dichloromethane was allowed to stand for 6 hours, and poured onto ice and extracted with dichloromethane. The combined extracts were worked up as in Example 32 to yield 21.0 g of orange oil. Proton nuclear magnetic resonance ($\delta$[ppm], CDCl$_3$) 90 MHz: 1.24 (t, 3H); 2.83 (t, 2H); 3.61 (t, 2H); 4.14 (q, 2H); [6.97 (dd, 1H) and 7.41 (m, 2H) aromatic H's].

EXAMPLE 34

3-[[5-(4-Chlorophenyl)-1,2,3-thiadiazol-4-yl]thio]-propanoic acid, ethyl ester

A mixture of 29.5 g of 2-[2-(4-chlorophenyl)-1-thioxoethyl]hydrazinecarboxylic acid, methyl ester, 20.5 g of ethyl acrylate, 300 ml of benzene and 1 ml of triethylamine was heated at reflux for 18 hours and then concentrated in vacuo. The oily residue was chromatographed on a dry column of silica gel, eluting with dichloromethane. The desired fractions were combined and treated as described in Example 30, giving 20.5 g of [Z(and E)]-[1-[(3-ethoxy-3-oxopropyl)thio]-2-(4-chlorophenyl)ethylidene]hydrazinecarboxylic acid, methyl ester.

A mixture of 11.92 g of the above compound, 9 g of thionyl chloride and 200 ml of dichloromethane was allowed to stand for 15 hours, then poured onto ice and extracted twice with ether. The extracts were combined, washed with 0.1N sodium hydroxide twice, water and saturated sodium chloride, dried and evaporated. The resulting oil was dissolved in dichloromethane and evaporated onto 50 g of silica gel. This silica gel was poured onto a column of silica gel packed in petroleum ether and then eluted under slight pressure, with a gradient of 0–20% ethyl acetate in petroleum ether giving an oil. This oil was crystallized from diisopropyl ether, giving 8.3 g of the desired compound as ivory cubes, mp 71.5°–73.5° C. Proton nuclear magnetic resonance ($\delta$[ppm], CDCl$_3$) 90 MHz: 1.24 (t, 3H, J=7.0 Hz, CH$_3$); 2.78 (t, 2H, J=7.0 Hz, CH$_2$CO$_2$); 3.56 (t, 2H, SCH$_2$); 4.10 (q, 2H, OCH$_2$); 7.50 (A$_2$B$_2$ quartet, 4H, C$_6$H$_4$). Infrared absorption spectrum (KBr pellet): 1725(s); 1590(w); 1400(w); 1370(w); 1280(w); 1250(w); 1220(m); 1175(m); 1150(m); 1090(m); 1010(m); 930(m); 830(m).

EXAMPLE 35

3-[[5-(4-Fluorophenyl)-1,2,3-thiadiazol-4-yl]thio]-propanoic acid, ethyl ester

A mixture of 36.3 g of 2-[2-(4-fluorophenyl)-1-thioxoethyl]hydrazinecarboxylic acid, methyl ester, 20 g of ethyl acrylate, 250 ml of benzene and 1 ml of triethylamine was heated at reflux for 18 hours, cooled and concentrated in vacuo. The oily residue was taken up in dichloromethane, filtered through a bed of diatomaceous earth with additional solvent and evaporated in vacuo. The residual oil was chorm;atographed on a dry column of silica gel, eluting with dichloromethane. The active fractions were combined and concentrated in vacuo, giving [Z(and E)]-[1-[(3-ethoxy-3-oxopropyl)- thio]-2-(4-fluorophenyl)ethylidene]hydrazinecarboxylic acid, methyl ester as a colorless oil.

A solution of 28 g of the above compound, 20.3 g of thionyl chloride and 150 ml of dichloromethane was reacted as described in Example 34, giving 20.6 g of the desired product as ivory needles, mp 76.5°–77.5° C. Proton nuclear magnetic resonance (δ[ppm], CDCl$_3$) 90 MHz: 1.23 (t, 3H, J=7.0 Hz, CH$_3$); 2.80 (t, 2H, J=7.0 Hz, CH$_2$CO$_2$); 3.56 (t, 2H, SCH$_2$); 4.13 (q, 2H, OCH$_2$); [7.20 (dd, 2H, J$_{H-F}$=8.0 Hz; J$_{H-H}$=8.0 Hz) and 7.61 (dd, 2H, J$_{H-F}$=5.5 Hz) (C$_6$H$_4$)]. Infrared absorption spectrum (KBr pellet): 1730(s); 1605(w); 1520(m); 1475(m); 1440(w); 1410(w); 1375(w); 1355(w); 1255(w); 1240(m); 1220(m); 1200(m); 1050(w); 1020(w); 930(m); 830(m).

EXAMPLE 36

3-[[5-(3-Methoxyphenyl)-1,2,3-thiadiazol-4-yl]thio]-propanoic acid ethyl ester

[1-[(3-Ethoxy-3-oxopropyl)thio]-2-(3-methoxyphenyl)ethylidene]hydrazinecarboxylic acid, methyl ester was prepared from 2-[2-(3-methoxyphenyl)-1-thioxoethyl]hydrazinecarboxylic acid, methyl ester.

A mixture of the 36.3 g of the above compound in dichloromethane was treated with 25.0 g of thionyl chloride, stored at 30° C. for 8 hours and then poured onto chipped ice. The product was extracted three times with ether. The extracts were combined, washed with water twice, 0.1N sodium hydroxide twice, water, saturated sodium chloride and dried. The solution was evaporated onto silica gel which was poured onto a silica gel column and eluted with a gradient of 0–15% ethyl acetate in hexane. The desired fractions were combined to give 18.0 g of the desired compound as a light orange oil. Proton nuclear magnetic resonance (δ[ppm], CDCl$_3$) 90 MHz: 1.23 (t, 3H, J=7.0 Hz, CH$_3$); 2.79 (t, 2H, J=7.0 Hz, CH$_2$CO$_2$); 3.55 (t, 2H, SCH$_2$); 3.82 (s, 3H, OCH$_3$); 4.10 (q, 2H, OCH$_2$); 6.80-7.55 (m, 4H, C$_6$H$_4$). Infrared absorption spectrum (neat): 1725(s); 1590(m); 1575(m); 1495(m); 1458(m); 1450(m); 140(m); 1370(m); 1345(m); 1295(m); 1280(m); 1245(m); 1185(m); 1160(m); 1051(m); 1006(m); 936(m); 860(m); 780(m).

EXAMPLE 37

3-[[5-[3-(Trifluoromethyl)Phenyl]-1,2,3-thiadiazol-4-yl]thio]propanoic acid, methyl ester A suspension of 29.3 g of 2-[1-thioxo-2-[3-(trifluoromethyl)phenyl]ethyl]hydrazinecarboxylic acid, methyl ester, was reacted with methyl acrylate, triethylamine and benzene as described in Example 35, giving [Z(and E)]-[1-[(3-methoxy-3-oxopropyl)thio]-2-[3-(trifluoromethyl)phenyl]ethylidene]hydrazinecarboxylic acid, methyl ester.

A solution of 37.8 g of the above compound in 250 ml of dichloromethane was treated with 18 g of thionyl chloride. After standing for 3 hours the solvent was removed in vacuo, the residue taken up in ether, washed with 0.1N sodium hydroxide twice, then saturated sodium chloride, dried and evaporated on 125 g of silica gel. This silica gel was poured onto a column of silica gel packed in petroleum ether and then eluted with a gradient of 0–10% ethyl acetate in petroleum ether, giving 17.5 g of the desired product as an orange oil. Proton nuclear magnetic resonance (δ[ppm], CDCl$_3$) 90 MHz: 2.86 (t, 2H, J=7.0 Hz, CH$_2$CO$_2$); 3.57 (t, 2H, SCH$_2$); 3.66 (s, 3H, OCH$_3$); 7.55–7.85 (m, 4H, C$_6$H$_4$).

EXAMPLE 38

3-[[5-(Phenylmethyl)-,1,2,3-thiadiazol-4-yl]thio]-propanoic acid, methyl ester

A suspension of 22.4 g of 2-(aminocarbonyl)hydrazide benzenepropanethioic acid in 300 ml of dry benzene was treated with 25 ml of methyl acrylate followed by 1 ml of triethylamine. After 2 hours the solution was concentrated in vacuo, the resulting oil was taken up in dichloromethane and chromatographed on silica gel, eluting with the same solvent. The desired fractions were combined and concentrated in vacuo, giving 27.9 g of (Z)-3-[[1-[(aminocarbonyl)hydrazinone]-3-phenylpropyl]thio]propanoic acid, methyl ester as a yellow oil.

A solution of 20.7 g of the above compound in 150 ml of chloroform was reacted with thionyl chloride as described in Example 22, giving 10 g of the desired compound as an orange oil. Proton nuclear magnetic resonance (δ[ppm], CDCl$_3$) 90 MHz: 2.85 (t, 2H, J=7.0 Hz, CH$_2$CO$_2$); 3.57 (t, 2H, SCH$_2$); 3.65 (s, 3H, OCH$_3$); 4.31 (s, 2H, CH$_2$C$_6$H$_5$); 7.30 (m, 5H, C$_6$H$_5$). Infrared absorption spectrum (neat): 1735(s); 1495(w); 1435(m); 1355(m); 1245(s); 1220(m); 1200(m); 1170(m); 705(m).

EXAMPLE 39

3-[[5-(Phenylthio)-1,2,3-thiadiazol-4-yl]thio]propanoic acid, ethyl ester

A solution of 40 g of 2-[2-(phenylthio)-1-thioxoethyl]-hydrazinecarboxylic acid, methyl ester, 20.5 g of ethyl acrylate, 2 ml of triethylamine and 300 ml of benzene was heated at reflux for 12 hours, then cooled and concentrated in vacuo. The residue was dissolved in dichloromethane, filtered through hydrous magnesium silicate, washing with the same solvent and evaporated to an oil, giving 33.5 g of [Z(and E)]-[1-[(3-ethoxy-3-oxopropyl)thio]-2-(phenylthio)ethylidene]hydrazinecarboxylic acid, methyl ester.

A 33 g portion of the above compound and thionyl chloride in 250 ml of dichloromethane was allowed to stand for 6 hours, then poured into ice and extracted three times with ether. The extracts were combined, washed with 0.1N sodium hydroxide twice, water, saturated sodium chloride, dried and evaporated onto 100 g of neutral alumina. The alumina was applied to a column of neutral alumina packed in petroleum ether. The column was eluted with a gradient of 0–10% ethyl acetate in petroleum ether. The active fractions were combined giving 28 g of the desired product as an orange oil. Proton nuclear magnetic resonance (δ[ppm], CDCl$_3$) 90 MHz: 1.27 (t, 3H, J=7.2 Hz, CH$_3$CH$_2$O); 2.79 (t, 2H, J=7.0 Hz, CH$_2$CO$_2$); 3.44 (t, 2H, SCH$_2$); 4.17 (q, 2H, OCH$_2$); 7.40–7.70 (bs, 5H, C$_6$H$_5$). Infrared absorption spectrum (neat): 1735(s); 1575(m); 1475(m); 1435(m); 1385(m); 1370(m); 1345(m); 1210(s); 1185(s); 1150(s); 1055(m); 1020(m); 930–925(m); 750(s); 690(s).

EXAMPLE 40

(Racemic)-3-[[5-(Tetrahydro-2H-Pyran-2-yl)-1,2,3-thiadiazol-4-yl]thio]propanoic acid, methyl ester 2-[2-(Tetrahydro-2H-pyran-2-yl)-1-thioxoethyl]hydrazinecarboxylic acid, methyl ester was converted to [Z(and E)]-[1-[(3-methoxy-3-oxopropyl)thio]-2-[(3-tetrahydro-2H-pyran-2-yl)ethylidene]hydrazinecarboxylic acid, methyl ester as described in Example 35.

The above compound was reacted as described in Example 37, giving the desired product as an orange oil.

Proton nuclear magnetic resonance (δ[ppm], CDCl$_3$) 300 MHz: 1.50–2.20 [m, 6H, (CH$_2$)$_3$CH$_2$O]; 2.80 (t, 2H, J=7.0 Hz, CH$_2$CO$_2$); 3.45–3.60 (m, 2H, CH$_2$O); 3.55 (t, 2H, SCH$_2$); 3.70 (s, 3H, CH$_3$O); 5.22 (dd, 1H, J=7.0 Hz; 6.0 Hz, CHO). Infrared absorption spectrum (neat): 1742(s); 1440(s); 1360(s); 1295(m); 1245(m); 1220(m); 1200(m); 1170(m); 1150(m); 935(m).

EXAMPLE 41

4-(ethylthio)-1,2,3-thiadiazole

A mixture of 54.1 g of methyl hydrazinecarboxylate, 61.8 g of distilled ethyl dithioacetate and 500 ml of chloroform was heated at reflux for 3 hours, then evaporated in vacuo. The residue was dissolved in 500 ml of ether:dichloromethane (1:1), washed with water twice, then saturated sodium chloride, dried and concentrated in vacuo. The residue was suspended in cold hexane:ether (1:1) and the solid collected and recrystallized from methylcyclohexane, giving 53 g of [Z(and E)]-[1-(ethylthio)ethylidene]hydrazinecarboxylic acid, methyl ester as ivory colored needles, mp 87°–88.5° C.

A solution of 1.8 g of the above compound in 10 ml of dry dichloromethane was treated with 5 ml of thionyl choride, allowed to stand 3 hours and concentrated in vacuo. The resulting oil was dissolved in a small amount of dichloromethane and applied to six 2000μ×20 cm×20 cm silica gel preparative TLC plates. The plates were eluted with dichloromethane and the active band worked up to give a red oil. This oil was taken up in a small amount of dichloromethane and filtered through neutral alumina with the same solvent, giving 295 mg of the desired product as a light yellow oil. Proton nuclear magnetic resonance (δ[ppm], CDCl$_3$) 90 MHz: 1.38 (t, 3H, J=7.0 Hz, CH$_3$); 3.17 (q, 2H, SCH$_3$); 8.25 (s, 1H, H-5). Infrared absorption spectrum (neat): 3120(m); 1415(s); 1265–1245(s); 1210(s); 950(s); 884(s); 820–720(m).

EXAMPLE 42

5-(1,1-Dimethylethyl)-4-(phenylthio)-1,2,3-thiadiazole

A solution of 65.5 g of hydrazinecarboxylic acid, methyl ester, 150 ml of dry pyridine and 500 ml of dry dichloromethane was stirred at 0° C. and 100 g of distilled t-butylacetyl chloride was added dropwise. After 2 hours at 0°–5° C. the solvent was removed in vacuo. The residue was taken up in 1.2 liters of ethyl acetate, washed with saturated sodium chloride and filtered through a bed of hydrous magnesium silicate with additional ethyl acetate. The filtrate was concentrated and the solid recrystallized from diisopropyl ether, giving 130 g of 2-(3,3-dimethyl-1-oxobutyl)hydrazinecarboxylic acid, methyl ester as white platelets, mp 83°–84.5° C.

A solution of 23 g of the above compound, 26.1 g of phosphorous pentachloride and 250 ml of chloroform containing 5 drops of dimethylformamide was heated at reflux for 4 hours, then cooled and concentrated in vacuo. The oily residue was azeotropically distilled twice with toluene under vacuum, then dissolved in 150 ml of dry tetrahydrofuran and added dropwise to a freshly prepared suspension of sodium thiophenoxide in tetrahydrofuran. After 3 hours the solution was concentrated in vacuo, the residue dissolved in 500 ml of water and extracted three times with ethyl acetate. The extracts were combined, washed with 0.1N sodium hydroxide twice, then saturated sodium chloride and dried. The resulting oil was dissolved in petroleum ether, applied to a chromatographic column on a Waters Prep 500A and eluted with 4.5 liters of petroleum ether to remove low polarity components. The column was then eluted with 4 liters of 1% methanol in dichloromethane, giving 17.5 g of [Z(and- E)]-[3,3-dimethyl-1-(phenylthio)butylidene]hydrazinecarboxylic acid, methyl ester as a light orange oil.

A solution of 14 g of the above compound, 8.85 g of thionyl chloride and 250 ml of chloroform was heated at reflux for 8 hours, then cooled and concentrated in vacuo. The resulting oil was dissolved in a small amount of benzene and applied to a column of silica gel packed in benzene. The active fractions were collected, giving 8.8 g of the desired product as a yellow oil. Proton nuclear magnetic resonance (δ[ppm], CDCl$_3$) 90 MHz: 1.58 (s, 9H, t-butyl); 7.29 (bs, 5H, C$_6$H$_5$). Infrared absorption spectrum (neat): 1585(m); 1480(s); 1442(m); 1370(m); 1250(m); 1219(m); 1180(m); 1028(w) 926(s); 745(m); 710(s); 695(s).

EXAMPLE 43

5-Phenyl-4-(phenylthio)-1,2,3-thiadiazole

A mixture of 43.8 g of phosphorous pentachloride in 350 ml of dry dichloromethane was treated dropwise with a solution of 44.5 g of 2-(phenyl-1-oxoethyl)hydrazinecarboxylic acid, methyl ester in 200 ml of dry dichloromethane. After refluxing for 6 hours, the solvent was removed in vacuo and the residue was azeotropically distilled twice with 350 ml portions of toluene. The residue was then dissolved in 200 ml of dry tetrahydrofuran and saved.

A suspension of 4.7 g of sodium hydride in 350 ml of dry tetrahydrofuran was treated dropwise with 6.75 g of dry methanol, then 23.2 g of thiophenol was added. After one hour the tetrahydrofuran solution of crude hydrazonyl chloride was added dropwise at 0°–5° C. over a 30 minute period. After 2 hours at room temperature the solvent was removed in vacuo and the mixture was partitioned between ethyl acetate and water. The aqueous layer was extracted twice with ethyl acetate, all organic layers were combined, washed with saturated sodium chloride and dried. The resulting oil was evaporated onto 125 g of silica gel. This silica gel was applied to a column of silica gel packed in petroleum ether and eluted with a gradient of 0–50% ethyl acetate in petroleum ether. The desired fractions were collected giving an oil which was crystallized from isopropyl ether, giving 40 g of (Z)-[2-phenyl-1-phenylthio)ethylidene]hydrazinecarboxylic acid, methyl ester as yellow needles, mp 67.5°–70° C..

A solution of (Z)-[2-phenyl-1-(phenylthio)ethylidene]hydrazinecarboxylic acid, methyl ester in 450 ml of dry dichloromethane was treated with 29.7 g of thionyl chloride. This mixture ws refluxed for one hour, then poured into chipped ice and extracted three times with ether. The extracts were combined, washed with 0.1N sodium hydroxide twice, water and saturated sodium chloride and dried. This material was evaporated onto 100 g of silica gel which was then poured onto a column of silica gel packed in petroleum ether. The column was eluted with a gradient of 20–60% dichloromethane in petroleum ether, giving 35 g of the desired compound as an orange oil. Proton nuclear magnetic resonance (δ[ppm], CDCl$_3$) 90 MHz: 7.28 (bs, 5H, C$_6$H$_5$); 7.30–7.65 (m, 5H, C$_6$H$_5$). Infrared absorption spectrum (neat): 1580(m); 1475(s); 1440(s); 1286(w); 1265(m); 1255(m); 1240(w); 1025(w); 1005(w); 985(w); 935(m); 915(m); 805(m); 765(m); 745(s); 695(s).

EXAMPLE 44

4-(Methylthio)-1,2,3-thiadiazole-5-carboxylic acid, ethyl ester

A mixture of 107.5 g of freshly distilled ethyl 3-thioxo-N-piperidinepropionate, 100.0 g of iodomethane and 500 ml of anhydrous ether was stirred for 24 hours. The solid was collected, washed with ether and dried in vacuo, giving 155 g of 1-[1-(methylthio)]-2-[ethoxycarbonyl]ethylidene]piperidinium iodide.

A suspension of 140 g of the above compound in 450 ml of anhydrous ethanol was treated with gaseous hydrogen sulfide for 5 hours, then allowed to stand 24 hours. The solvent was removed in vacuo, the residue suspended in 700 ml of dry ether and filtered. The filter cake was washed with ether, the wash and filtrate combined and concentrated in vacuo and then distilled giving 67.7 g of 2-(ethoxycarbonyl)ethane(dithioic acid), methyl ester as an orange liquid, bp 91°–92° C. (0.1 mmHg).

A mixture of 35.8 g of the above compound, 19.81 g of hydrazinecarboxylic acid, methyl ester and 250 ml of dichloromethane was heated at reflux for 8 hours, then concentrated in vacuo. The resulting oil was taken up in ether:dichloromethane (1:1), washed twice with water, dried and concentrated in vacuo. This residue was dissolved in ether, 56.4 g of methyl iodide was added, the mixture stored for 48 hours and then concentrated in vacuo. The oily residue was dissolved in 75 ml of acetone, 280 ml of 1N sodium carbonate was added and this mixture was extracted three times with ether. The extracts were combined, and worked up giving 55.0 g of [E(and Z)]-[1-(methylthio)-2(ethoxycarbonyl)ethylidene]hydrazinecarboxylic acid, methyl ester as an orange oil.

A solution of 16 g of the above compound in 150 ml of dichloromethane was treated with 17.9 g of thionyl chloride, allowed to stand 4 hours, poured onto ice and then extracted three times with ether. The extracts were combined, washed with water, 0.1N sodium hydroxide and water and then concentrated in vacuo. The resulting oil was purified on a flash chromatography column of alumina, eluting with a 0–10% ethyl acetate in petroleum ether gradient. The active fractions were combined, concentrated in vacuo and crystallized from diisopropyl ether, giving 7.0 g of the desired product as white cubic crystals, mp 64.5°–65.5° C.. Proton nuclear magnetic resonance (δ[ppm], CDCl$_3$) 90 MHz: 1.37 (t, 3H, J=7.0 Hz, CH$_3$CH$_2$O); 2.87 (s, 3H, SCH$_3$); 4.39 (q, 2H, OCH$_2$). Infrared absorption spectrum (KBr pellet): 1710(s); 1470(w); 1440(w); 1430(w); 1365(w); 1320(w); 1305(s); 1175(s); 1085(s); 1010(m); 970(m).

EXAMPLE 45

4-(Methylthio)-5-(2-thienyl)-1,2,3-thiadiazole

2-[2-(2-Thienyl)-1-thioxoethyl]hydrazinecarboxylic acid, methyl ester was chromatographed on silica gel, eluting with dichlorme thane giving [E(and Z)]-[1-(methylthio)-2-(2-thienyl)ethylidene]hydrazinecarboxylic acid, methyl ester.

A solution of 24.4 g of the above compound in 150 ml of dichloromethane was stirred with 25.0 g of thionyl chloride. After 3 hours the mixture was poured onto ice and basified to pH 9 with 0.1N sodium hydroxide. This suspension was extracted with dichloromethane twice, the extracts combined, dried and concentrated in vacuo. The resulting oil was taken up in 250 ml of dichloromethane, evaporated onto silica gel which was then applied to a column of silica gel packed in petroleum ether and eluted with a gradient of 0–20% dichloromethane in petroleum ether. The desired fractions were pooled and evaporated, giving an oil which was crystalized from diisopropyl ether, giving 11 g of the desired product as yellow crystals, mp 49°–49.5° C. Proton nuclear magnetic resonance (δ[ppm], CDCl$_3$) 90 MHz: 2.85 (s, 3H, SCH$_3$); [6.96 (dd, 1H) and 7.41 (m, 2H) (C$_4$H$_3$S)]. Infrared absoprtion spectrum (KBr pellet): 1435(m); 1420(m); 1390(s); 1352(m); 1250(s); 220(m); 1195(m); 1160(m); 920(m); 705(s).

EXAMPLE 46

5-(4-Methoxyphenyl)-4-(methylthio)-1,2,3-thiadiazole

A mixture of 70.7 g of (4-methoxyphenyl)ethanedithioic acid, methyl ester, 31.0 g of hydrazinecarboxylic acid, methyl ester, and 500 ml of dichloromethane was heated at reflux for 8 hours, and then concentrated in vacuo. The resulting oil was taken up in dichloromethane and applied to a column of silica gel. The column was eluted with a gradient of 0–2% methanol in dichloromethane and the desired fractions pooled and concentrated. The yellow liquid was used as obtained.

A mixture of 55 g of [E(and -Z)]-[1-(methylthio)2-(4-methoxyphenyl)ethylidene]hydrazinecarboxylic acid, methyl ester in 350 ml of dichloromethane was treated with 29.5 g of thionyl chloride. This mixture was allowed to stand for 10 hours, then poured onto ice and extracted thrice with dichloromethane. The extracts were combined, washed with 2% sodium hydroxide twice, water and saturated sodium chloride, dried and evaporated. The residue was crystallized from diisopropyl ether, giving 40.5 g of the desired product as off-white needles, mp 60.5°–61° C. Proton nuclear magnetic resonance (δ[ppm], CDCl$_3$) 90 MHz: 2.81 (s, 3H, SCH$_3$); 3.86 (s, 3H, OCH$_3$); [7.02 (d, 2H, J=9.0 Hz) and 7.57 (d, 2H)(C$_6$H$_4$)]. Infrared absorption spectrum (KBr pellet): 1605(m); 1515(m); 1460(w); 1450(w); 1435(m); 1400(m); 1300(m); 1265(m); 1245(s); 1210(w); 1175(m); 1022(s); 930(m); 830(s).

EXAMPLE 47

4-(Methylthio)-5-[3-(trifluoromethyl)phenyl-1,2,3thiadiazole

A solution of 11.6 g of 3-[[5-[3-(trifluoromethyl)phenyl]-1,2,3-thiadiazol-4-yl]thio]propanoic acid, methyl ester in 100 ml of dry methanol was treated with 32 ml of 1M methanolic sodium methoxide. After standing one hour, the solvent was removed in vacuo, the residue taken up in dry methanol, filtered and then concentrated. The oil was triturated with ether giving a solid which was collected and dried in vacuo, giving 6.8 g of 5-[3-(trifluoromethyl)phenyl]-1,2,3-thiadiazole-4-thiol, monosodium salt as a yellow powder, mp >200° C..

A solution of 5.69 g of the above compound in 25 ml of methanol was treated with 7.1 g of methyl iodide. After standing for 2 hours, the solvent was removed in vacuo, the residue taken up in 75 ml of dichloromethane and filtered through a bed of hydrous magnesium silicate with additional solvent. The filtrate was evaporated giving the desired compound as a light orange oil. Proton nuclear magnetic resonance (δ[ppm], CDCl$_3$) 90 MHz: 2.85 (s, 3H, SCH$_3$); 7.45–8.00 (m, 4H, C$_6$H$_4$). Infrared absorption spectrum (neat): 1495(w); 1465(w);

1430(w); 1415(w); 1325(s); 1250(s); 1170(s); 1125(s); 1070(m); 1005(w); 935(m); 895(m); 800(m); 695(m).

EXAMPLE 48

3-[5-(4-Methylphenyl)-1,2,3-thiadiazol-5-yl]thio] acetic acid, ethyl ester

A suspension of 13.8 g of 3-[[5-(4-methylphenyl)-1,2,3-thiadiazol-4-yl]thio]propanoic acid, ethyl ester in 250 ml of dry ethanol was treated with 200 ml of 1M potassium ethoxide in ethanol. After standing 1.5 hours, the solvent was removed in vacuo to about 100 ml and 400 ml of anhydrous ether was added. The solid was collected, washed with ether, dissolved in methanol and filtered. The filtrate was concentrated to a small volume and then diluted with 400 ml of anhydrous ether. The solid was collected and dried in vacuo, giving 11.5 g of 5-(4-methylphenyl)-1,2,3-thiadiazole-4-thiol, monopotassium salt as a yellow solid, mp >125° C. (dec.).

A solution of 4.92 g of the above compound in 50 ml of dry methanol was treated with 3.45 g of ethyl bromoacetate, stirred for 12 hours and the solvent removed in vacuo. The residue was suspended in ether, filtered and washed with ether. The combined filtrate and wash was concentrated in vacuo, giving an oil. This oil was taken up in dichloromethane and evaporated onto 20 g of silica gel. This gel was poured onto a dry column of silica gel and then eluted with 15% ethyl acetate in hexane. The desired fraction was concentrated giving an oil which was crystallized from petroleum ether, giving 5 g of the desired product as ivory cubes, mp 60°-60.5° C. Proton nuclear magnetic resonance ($\delta$[ppm], CDCl$_3$) 90 MHz: 1.21 (t, 3H, J=7.0 Hz, CH$_3$); 2.42 (s, 3H, CH$_3$); 4.10 (s, 2H, SCH$_2$); 4.17 (q, 2H, CH$_2$O); [7.32 (d, 2H, J=8.0 Hz) and 7.55 (d, 2H)(C$_6$H$_4$)]. Infrared absorption spectrum (KBr pellet): 1736(s); 1515(w); 1475(w); 1440(w); 1400(w); 1380(w); 1370(w); 1315(s); 1290(w); 1250(w); 1225(w); 1175(s); 1168(s); 1025(m); 930(m); 815(m).

EXAMPLE 49

5-[4-(1,1-Dimethylethyl)phenyl]-4-(ethylthio) 1,2,3-thiadiazole

A solution of 15.9 g of 3-[[5-[4-(1,1-dimethylethyl)phenyl]-1,2,3-thiadiazol-4-yl]thio]propanoic acid, ethyl ester in 75 ml of anhydrous ethanol was treated with 105 ml of 0.5M potassium ethoxide in ethanol. After 3 hours the solvent was partially removed in vacuo and 200 ml of anhydrous ether was added. The resulting solid was collected, washed with ether, redissolved in methanol, filtered and the filtrate concentrated to 10-15 ml. A 250 ml portion of anhydrous ether was added and the solid was collected and dried in vacuo, giving 13 g of 5-[4-(1,1-dimethylethyl)phenyl]-1,2,3-thiadiazol-4-thiol, potassium salt as a yellow solid, mp >150° C.

A mixture of 865 mg of the above compound in 25 ml of ethanol was treated with 940 mg of ethyl iodide, then stirred for one hour and concentrated in vacuo. The residue was taken up in ether, filtered and concentrated to an oil. This oil was purified on thick layer chromatography plates, eluting with dichloromethane, giving 755 mg of the desired compound as a yellow oil. Proton nuclear magnetic resonance ($\delta$[ppm], CDCl$_3$) 90 MHz: 1.37 (s, 9H, t-butyl); 1.39 (t, 3H, J=7.0 Hz, CH$_3$); 3.35 (q, 2H, SCH$_3$); 7.54 (s, 4H, C$_6$H$_4$). Infrared absorption spectrum (neat): 1610(w); 1520(w); 1475(w); 1460(w); 1445(w); 1405(w); 1365(w); 1270(s); 1175(s); 936(s); 820(s).

EXAMPLE 50

5-[4-(1,1-Dimethylethyl)phenyl]-4-(2-propenylthio)-1,2,3-thiadiazole

A solution of 1.45 g of 5-[4-(1,1-dimethylethyl)-phenyl-1,2,3-thiadiazole-4-thiol, potassium salt in 50 ml of ethanol was stirred overnight with 3.0 g of allyl bromide. The solvent was removed in vacuo, the residue taken up in ether, filtered and concentrated in vacuo. The residual oil was dissolved in a small amount of dichloromethane and purified on thick layer silica gel plates, eluting with the same solvent. The active fraction gave 1.225 g of the desired compound as a yellow oil. Proton nuclear magnetic resonance ($\delta$[ppm], CDCl$_3$) 90 MHz: 1.39 (s, 9H, t-butyl); 3.98 (bd, 2H, SCH$_2$); 5.05 (bd, 1H, CH=); 5.20 (bd, 1H, =CH); 5.87 (m, 1H, CH$_2$CH=); 7.55 (s, 4H, C$_6$H$_4$). Infrared absorption spectrum (neat): 1640(w); 1615(w); 1525(w); 1480(w); 1475(w); 1450(w); 1410(w); 1370(w); 1270(w); 930(s); 820(s).

EXAMPLE 51

[[5-[4-(1,1-Dimethylethyl)phenyl]-1,2,3-thiadiazol-4-yl]thio]acetic acid ethyl ester A solution of 2.9 g of 5-[4-(1,1-dimethylethyl)-phenyl]-1,2,3-thiadiazole-4-thiol, potassium salt in 50 ml of ethanol was stirred overnight with 1.67 g of ethyl bromoacetate, then concentrated in vacuo. The residue was taken up in ether, filtered and evaporated in vacuo. The oily residue was dissolved in dichloromethane and purified as described in Example 50, giving an oil which was crystallized from methylcyclohexane, giving 2.8 g of the desired compound as white needles, mp 62.5°-63.5° C. Proton nuclear magnetic resonance ($\delta$[ppm], CDCl$_3$) 90 MHz: 1.21 (t, 3H, J=7.0 Hz, CH$_3$); 1.37 (s, 9H, t-butyl); 4.11 (s, 2H, SCH$_2$); 4.15 (q, 2H, CH$_2$O); 7.55 (s, 4H, C$_6$H$_4$). Infrared absorption spectrum (KBr pellet): 1739(s); 1606(w); 1520(w); 1480(w); 1445(w); 1385(w); 1365(w); 1305(s); 1175(s); 1040(w); 935(s); 840(s).

EXAMPLE 52

2-Methyl-2-[[5-(phenylmethyl)-1,2,3-thiadiazol-4-yl]thio]propanoic acid, ethyl ester A solution of 1.99 g of 5-(phenylmethyl)-1,2,3-thiadiazole-4-thiol, sodium salt in 30 ml of ethanol was stirred overnight with 1.96 g of ethyl 2-bromoisobutyrate and then concentrated in vacuo. The residue was taken up in ether, filtered, and evaporated in vacuo. The oily residue was purified as described in Example 50, giving a yellow oil. Proton nuclear magnetic resonance ($\delta$[ppm], CDCl$_3$) 90 MHz: 1.22 (t, 3H); 1.67 (s, 2 CH$_3$'s); 4.12 (q, 2H); 4.31 (s, CH$_2$); 7.30 (6s, SH).

EXAMPLE 53

3-[(5-Phenyl-1,2,3-thiadiazol-4-yl)thio]propanenitrile

A mixture of 22.4 g of 2-(2-phenyl-1-thioxoethyl)hydrazinecarboxylic acid, methyl ester, 10.6g of acrylonitrile, 1.0 ml of triethylamine and 100 ml of benzene was heated at reflux for 18 hours, then cooled and concentrated in vacuo. The resulting oil was purified by chromatography, giving [Z(and E)]-[1-[(2-cyanoethyl)thio]-2-phenylethylidene]hydrazinecarboxylic acid, methyl ester.

A solution of 21 g of the above ester, 20 ml of thionyl chloride and 150 ml of dichloromethane was heated at reflux for 3 hours, then cooled, poured onto chipped ice and extracted twice with ether. The extracts were combined, washed with water twice, 5% sodium bicarbonate twice, water, saturated sodium chloride, dried and concentrated in vacuo. The residual oil was chromatographed on silica gel, eluting with dichloromethane. The desired fractions were combined and evaporated, giving an oil which was taken up in dichloromethane and filtered through a bed of neutral alumina. Evaporation gave an oil which was crystallized from methylcyclohexane, giving the desired compound as ivory crystals, mp 63.5°–64.5° C. Proton nuclear magnetic resonance ($\delta$[ppm], CDCl$_3$) 90 MHz: 2.90 (t, 2H, J=6.5 Hz, CH$_2$CN); 3.55 (t, 2H, SCH$_2$); 7.54 (m, 5H, C$_6$H$_5$). Infrared absoprtion spectrum (KBr pellet): 2250(m); 1430(s); 1325(m); 1295(m); 1260(s); 1215(m); 1185(s); 935(s); 765(s); 695(s).

EXAMPLE 54

1,2,3-Thiadiazole-4-thiol, sodium salt

A mixture of 604 mg of 3-(1,2,3-thiadiazol-4-ylthio)propionic acid, ethyl ester, 150 mg of sodium methoxide and 15 ml of methanol was allowed to stand for 3 hours, then evaporated to 3–4 ml and 100 ml of ether was added. Chilling produced a solid which was collected, giving 333 mg of the desired compound. Proton nuclear magnetic resonance ($\delta$[ppm], CD$_3$OD) 90 MHz: 7.86(s, 1H, H-5).

EXAMPLE 55

5-Methyl-1,2,3-thiadiazole-4-thiol, sodium salt

A solution of 69.7 g of 3-[(5-methyl-1,2,3-thiadiazol-4-lyl)thio]propanoic acid, ethyl ester in 250 ml of dry ethanol was treated with 150 ml of 2N ethanolic sodium ethoxide. After 15 minutes, the mixture was concentrated to 75 ml and diluted with 750 ml of ether. The resulting solid was collected, washed with ether and dried, giving the desired product as a tan solid, mp >150° C. Proton nuclear magnetic resonance ($\delta$[ppm], CD$_3$OD) 90 MHz: 2.53 (s, 3H, CH$_3$). Infrared absorption spectrum (KBr pellet): 1620(m); 1580(m); 1420(s); 1375(w); 1240(s); 1200(s); 1190(m); 1125(m); 1061(s); 1000(m); 895(s).

EXAMPLE 56

5-Ethyl-1,2,3-thiadiazole-4-thiol, sodium salt

A solution of 12.3 g of 3-[(5-ethyl-1,2,3-thiadiazol-4-yl)thio]propanoic acid, ethyl ester in 100 ml of dry ethanol was treated with 60 ml of 0.76M ethanolic sodium ethoxide. After 30 minutes the solvent was removed in vacuo to a small volume and 500 ml of dry ether was added. The resulting solid was collected, washed with ether and dried, giving 7.5 g of the desired product, mp >150° C. Proton nuclear magnetic resonance ($\delta$[ppm], CD$_3$OD) 90 MHz: 1.31 (t, 3H, J=6.8 HZ, CH$_3$); 2.93 (q, 2H, CH$_2$). Infrared absorption spectrum (KBr pellet): 1615(m); 1580(m); 1455(m); 1415(s); 1380(m); 1240(s); 1185(s); 1135(m).

EXAMPLE 57

5-(1,1-Dimethylethyl)-1,2,3-thiadiazole-4-thiol, sodium salt

A solution of 11.5 g of 3-[[5-(1,1-dimethylethyl)- r 1,2,3-thiadiazol-4-yl]thio]propanoic acid, methyl ester in 100 ml of dry methanol was treated with 42 ml of 1M methanolic sodium methoxide. After standing one hour, the solvent was removed in vacuo to 20 ml and the suspension was diluted with dry ether. The solid was collected, washed with ether, dried, dissolved in 100 ml of methanol, filtered and concentrated to 10–15 ml. The concentrate was diluted with t-butyl methyl ether and the solid collected and dried, giving 5.7 g of the desired compound as yellow needles, mp >200° C. Proton nuclear magnetic resonance ($\delta$[ppm], CD$_3$OD) 90 MHz: 1.55 (s, 9H, t-butyl). Infrared absorption spectrum (KBr pellet): 1605(w); 1450–1465, 1365(s); 1255(m); 1158(m); 928(s).

EXAMPLE 58

5-Phenyl-1,2,3-thiadiazole-4-thiol, potassium salt

A solution of 1.8 g of 3-[(5-phenyl-1,2,3-thiadiazol-4-yl)thio]propanoic acid, ethyl ester in 20 ml of anhydrous ethanol was treated with 10 ml of 0.665M ethanolic potassium ethoxide. After 3 hours the solvent was removed in vacuo and the residue suspended in anhydrous ether. The solid was collected, giving 1.3 g of the desired compound as yellow crystals. Proton nuclear magnetic resonance ($\delta$[ppm], CD$_3$OD) 90 MHz: [7.40 (m, 1H); 7.45 (m, 2H); 8.06(m, 2H);(C$_6$H$_5$)]. Infrared absorption spectrum (KBr pellet): 1598(w); 1499(w); 1405(w); 1262(m); 1195(s); 1127(m); 930–940; 760(s); 680–700(s).

EXAMPLE 59

5-(4-Methylphenyl)-1,2,3-thiadiazole-4-thiol, potassium salt

A suspension of 13.8 g of 3-[[5-(4-methylphenyl)-1,2,3-thiadiazol-4-yl]thio]propanoic acid, ethyl ester in 250 ml of dry ethanol was treated with 200 ml of 1M potassium ethoxide in ethanol. After 1.5 hours the solvent was evaporated in vacuo to about 100 ml and 400 ml of anhydrous ether was added. The resulting solid was collected, washed with ether, redissolved in methanol, filtered, concentrated to a small volume and diluted with 400 ml of anhydrous ether. The solid was collected and dried in vacuo, giving 11.5 g of the desired compound, mp >125° C. (dec.). Proton nuclear magnetic resonance ($\delta$[ppm], CD$_3$OD) 90 MHz: 2.35 (s, 3H, CH$_3$); [7.24 (d, 2H, J=8.5 Hz) and 8.05 (d, 2H)(C$_6$H$_4$)]. Infrared absorption spectrum (KBr pellet): 1605(w); 1520(m); 1400(s); 1265(m); 1195(s); 1135(m); 930(m); 835(s); 8.0(s).

EXAMPLE 60

5-[4-(1,1-Dimethylethyl)phenyl]-1,2,3-thiadiazole 4-thiol, potassium salt

A solution of 15.9 g of 3-[[5-[4-(1,1-dimethylethyl)phenyl]-1,2,3-thiadiazol-4-yl]thio]propanoic acid, ethyl ester in 75 ml of anhydrous ethanol was treated with 105 ml of 0.5M potassium ethoxide in ethanol. After 3 hours the solvent was partially evaporated, 200 ml of anhydrous ether was added, the solid was collected, washed with ether, redissolved in methanol, filtered and concentrated to about 10–15 ml. A 250 ml portion of ether was added and the solid collected and dried in vacuo, giving 13 g of the desired compound as a yellow solid. Proton nuclear magnetic resonance ($\delta$[ppm], CD$_3$OD) 90 MHz: 1.35 (s, 9H, t-butyl); [7.42 (d, 2H, J=8.5 Hz) and 8.12 (d, 2H)(C$_6$H$_4$)]. Infrared absorption spectrum (KBr pellet): 1605(w); 520(m); 1465(m); 1400(s); 1245–1270, 1170(s); 1130(m); 29(s); 820(s).

EXAMPLE 61

5-[3-(Trifluoromethyl)phenyl]-1,2,3-thiadiazole 4-thiol, sodium salt

A solution of 11.6g of 3-[[5-[3-(trifluoromethyl)-phenyl]-1,2,3-thiadiazol-4-yl]thio]propanoic acid, methyl ester in 100 ml of dry methanol was treated with 32 ml of 1M methanolic sodium methoxide. After one hour the solvent was removed in vacuo, the residue was suspended in ether and the solid collected. This solid was taken up in dry methanol, filtered and concentrated to an oil. The oil was triturated with dry ether and the solid collected and dried in vacuo, giving 6.8 g of the desired compound as a yellow powder, mp >200° C. Proton nuclear magnetic resonance ($\delta$[ppm], $CD_3OD$) 90 MHz: [7.55 (m, 2H); 8.20 (m, 1H) and 8.75 (m, 1H)($C_6H_4$)]. Infrared absorption spectrum (KBr pellet): 1605(w): 1442(m); 1375(m); 1300-1320, 1240(m); 1165-1180(s); 1110-1130(m); 1065(m); 1002(m); 920(s); 878(s); 794(s); 687(s).

What is claimed is:

1. A compound having the formula:

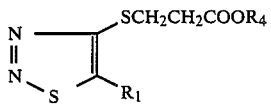

wherein $R_1$ is selected from the group consisting of hydrogen; alkyl($C_1$-$C_6$); (multisubstituted)phenyl wherein the substituents are selected from alkyl($C_1$-$C_6$), alkoxy($C_1$-$C_3$), chloro, fluoro and trifluoromethyl; naphthyl; thienyl; phenylthio; tetrahydropyranyl; benzyl; and —$COOC_2H_5$; and $R_4$ is alkyl($C_1$-($C_3$).

2. A compound having the formula:

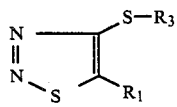

wherein $R_1$ from the group consisting of hydrogen; alkyl($C_1$-$C_6$); polyfluorinated alkyls ($C_1$-$C_6$); phenyl; (multisubstituted)phenyl wherein the substituents are selected from alkyl ($C_1$-$C_6$), alkoxy($C_1$-$C_3$), chloro, fluoro and trifluoromethyl; naphthyl; thienyl; phenylthio; tetrahydropyranyl; benzyl; and —$COOC_2H_5$; and $R_3$ is selected from the group consisting of alkyl(-$C_1$-$C_3$); phenyl; alkenyl($CC_3$-$C_6$) —$CH_2COOC_2H_5$; —$C(CH_3)_2COOC_2H_5$ and —$CH_2CH_2CN$.

3. A compound having the formula:

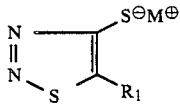

wherein $R1$ is selected from the group consisting of hydrogen; alkyl($C_1$-$C_6$); polyfluorinated alkyls($C_1$-$C_6$); phenyl; (multisubstituted)phenyl wherein the substituents are selected from alkyl($C_1$-$C_6$), alkoxy($C_1$-$C_3$), chloro, fluoro and trifluoromethyl; naphthyl; thienyl; phenylthio; tetrahydropyranyl: benzyl; and —$COOC_2H_5$: and M is sodium or potassium.

4. The compound according to claim 3, 1,2,3-thiadiazole-4-thiol, sodium salt.

5. The compound according to claim 3, 5-methyl-1,2,3-thiadiazole-4-thiol, sodium salt.

6. The compound according to claim 3, 5-ethyl-1,2,3-thiadiazole-4-thiol, sodium salt.

7. The compound according to claim 3, 5-(1,1-dimethylethyl)-1,2,3-thiadiazole-4-thiol, sodium salt.

8. The compound according to claim 3, 5phenyl1,2,3-thiadiazole-4-thiol, potassium salt.

9. The compound according to claim 3, 5-(4-methylphenyl)-1,2,3-thiadiazole-4-thiol, potassium salt.

10. The compound according to claim 3, 5-[4(1,1-dimethylethyl)phenyl]-1,2,3-thiadiazole-4-thiol, potassium salt.

11. The compound according to claim 3, 5-[3-(trifluoromethyl)phenyl]-1,2,3-thiadiazole-4-thiol, sodium salt.

* * * * *

UNITED STATES PATENT AND TRADEMARK OFFICE
CERTIFICATE OF CORRECTION

PATENT NO. : 4,803,280

DATED : February 7, 1989

INVENTOR(S) : Ving J. Lee et al.

It is certified that error appears in the above-identified patent and that said Letters Patent is hereby corrected as shown below:

Column 35, line 31, --phenyl;-- should be inserted before "(multisubstituted)".

Column 36, line 8, $--(C_3-C_6)--$ should be substituted for "$(CC_3-C_6)$".

Signed and Sealed this

Eighth Day of August, 1989

Attest:

DONALD J. QUIGG

Attesting Officer

Commissioner of Patents and Trademarks